(12) United States Patent
You et al.

(10) Patent No.: US 11,479,545 B2
(45) Date of Patent: Oct. 25, 2022

(54) COMPOSITIONS AND METHODS FOR INHIBITING PHENYL TRIAZOLE MLL1-WDR5 PROTEIN-PROTEIN INTERACTION

(71) Applicant: China Pharmaceutical University, Nanjing (CN)

(72) Inventors: Qidong You, Nanjing (CN); Xiaoke Guo, Nanjing (CN); Dongdong Li, Nanjing (CN); Weilin Chen, Nanjing (CN); Zhihui Wang, Nanjing (CN)

(73) Assignee: China Pharmaceutical University, Nanjing (CN)

( * ) Notice: Subject to any disclaimer, the term of this patent is extended or adjusted under 35 U.S.C. 154(b) by 0 days.

(21) Appl. No.: 17/078,052

(22) Filed: Oct. 22, 2020

(65) Prior Publication Data

US 2021/0139466 A1    May 13, 2021

Related U.S. Application Data

(63) Continuation of application No. PCT/CN2018/123500, filed on Dec. 25, 2018.

(51) Int. Cl.
| | |
|---|---|
| *C07D 405/12* | (2006.01) |
| *C07D 401/12* | (2006.01) |
| *C07D 249/06* | (2006.01) |
| *C07D 403/10* | (2006.01) |

(52) U.S. Cl.
CPC ......... *C07D 405/12* (2013.01); *C07D 249/06* (2013.01); *C07D 401/12* (2013.01); *C07D 403/10* (2013.01)

(58) Field of Classification Search
CPC .. C07D 405/12; C07D 249/06; C07D 401/12; C07D 403/10
USPC ........................................................ 514/218
See application file for complete search history.

(56) References Cited

U.S. PATENT DOCUMENTS

| 7,511,042 B2 * | 3/2009 | Cogan ....................... A61P 9/00 |
| | | 546/268.1 |
| 10,980,807 B2 | 4/2021 | Dai et al. |
| 11,174,250 B2 | 11/2021 | Al-Awar et al. |
| 2019/0112290 A1 | 4/2019 | Al-Awar et al. |
| 2021/0139466 A1 | 5/2021 | You et al. |

FOREIGN PATENT DOCUMENTS

| CN | 104844573 A | 8/2015 |
| CN | 105175284 B | 6/2017 |
| CN | 107382840 A | 11/2017 |
| WO | WO2011149827 A1 | 12/2011 |

OTHER PUBLICATIONS

PCT/CN2019079160 International Search Report, dated Nov. 26, 2019 (2 Pages).
Chinese Application CN201910139980 First Search dated Dec. 31, 2021 (1 Page).
Chinese Application CN201810365880 First Search dated Nov. 25, 2020 (2 Pages).
EP18916025.2 European Supplementary Search Report, dated Jul. 12, 2021 (8 pages).
Bolshan, et al., "Synthesis, Optimization, and Evaluation of Novel Small Molecules as Antagonists of WDR5-MLL Interaction," ACS Medicinal Chemisrty Letters, vol. 4, No. 3, Feb. 2013, pp. 353-357.
Li, Dongdong et al., "High-affinity Small Molevular Blockers of Mixed Lineage Leukemia 1 (MLL)-WDR5 Interaction Inhibit MLL1 Complez H3K4 Methyltransferase Activity," Euopean Journal Of Medicinal Chemistry, vol. 124, Aug. 20, 2016, pp. 480-489.
Li, Dongdong et al.," Structure-based Design and Synthesis of Small Molecular Inhibitors Disturbing the Interaction of MLL1-WDR5," European Journal of Medicinal Chemistry, vol. 118, Apr. 13, 2016, pp:1-8.
Getlik, Matthaus et al., " Structure-Based Optimization of a Small Molecule Antagonist of the Interaction Between WD Repeat-Containing Protein 5 (WDR5) and Mized-Lineage Leukemia 1 (MLL1)," Journal of Medicianl Chemistry, vol. 59, No. 6, Mar. 9, 2016, pp. 2478-2496.
PCT/CN2018123500 International Search Report, dated Mar. 11, 2019 (3 Pages).
Written Opinion of the International Search Authority for PCT/CN2018123500, dated Mar. 11, 2019 (5 pages, English).
Written Opinion of the International Search Authority for PCT/CN2019079160, dated Nov. 26, 2019 (4 pages, English).

* cited by examiner

*Primary Examiner* — Niloofar Rahmani
(74) *Attorney, Agent, or Firm* — Eversheds Sutherland (US) LLP

(57) ABSTRACT

The present disclosure relates to the field of medicinal chemistry, in particular to a phenyl triazole MLL1-WDR5 protein-protein interaction inhibitor (I) and a preparation method thereof, and pharmacodynamics experiments prove that the compound of the present disclosure has relatively strong MLL1-WDR5 protein-protein interaction inhibition activity.

10 Claims, 3 Drawing Sheets

COMPOSITIONS AND METHODS FOR INHIBITING PHENYL TRIAZOLE MLL1-WDR5 PROTEIN-PROTEIN INTERACTION

CROSS REFERENCE

The application is a continuation of PCT/CN2018123500, filed Dec. 25, 2018, which claims priority to CN201810365880, filed Apr. 23, 2018. The disclosures of which are herein incorporated by reference in their entireties.

BACKGROUND

Methylation of histones plays key roles in many biological processes and is the main content of study in epigenetic regulation field. Translocation and re-arrangement of the methyl transferase MLL1 gene for histone H3K4 can lead to mixed lineage leukemia (MLL1, acute myeloid leukemia and acute lymphoid leukemia). About 10% of leukemia patients have MLL1 gene rearrangement. After MLL1 gene arrangement, it fuses with other chaperone proteins to form fusion proteins, and the carcinogenic MLL fusion protein is expressed. The fusion protein can interact with RNA polymerase II (Pol II) related elongation factors to form the super elongation complex (SEC). The complex can lead to abnormal expression of the MLL1 regulated Hox gene, which causes series of serious consequences to induce MLL leukemia onset.

Rearrangement of the MLL1 gene occur on one allele and the wildtype MLL1 is still present. When the wildtype MLL1 allele is knocked out, the MLL fusion protein alone will not lead to leukemia, and the enzyme activity of the wildtype MLL1 is necessary for the MLL1 fusion protein to cause leukemia. Thus, specific inhibition of the wildtype MLL1 enzyme activity will cure leukemia.

Catalytic activity on H3K4 methylation by MLL1 alone is very weak and can only result in monomethylation; the catalytic activity improves greatly upon the formation of the MLL1 core catalytic complex, especially the catalytic activity on H3K4me2. The WIN motif on the C-terminus of the MLL binds to WDR5, RbBP5, Ash2L and DPY30 to form complexes. MLL1 interacts with WDR5 directly through the C-terminus WIN motif, to mediate the interaction between the catalytic domain of MLL1SET and other protein complexes. When WDR5 is knocked out, the level of H3K4me2/3 decreases and the Hox gene expression level decreases.

Thus, the use of small molecule to interfere the protein-protein interaction of MLL1-WDR5 is an effective method to inhibit MLL1 enzymatic activity and lower Hox and Meis-1 gene expression levels and to block the progression of leukemia.

DETAILED DESCRIPTION

The present disclosure is in the medicinal chemistry field, more specifically, is for a class of phenyl triazole MLL1-WDR5 protein-protein interaction inhibitor, its preparation and pharmaceutical uses. An aspect of the present disclosure comprises a small molecule compound that regulates MLL1-WDR5 protein-protein interactions, through interference of which, it inhibits the enzymatic activities of catalysis, down-regulates the methylation levels of H3K4, and gene expression levels of Hox and Meis-1 genes, which in turn to induce the apoptosis of leukemia cells for the applications of leukemia treatment. The structure of the compound in this disclosure is:

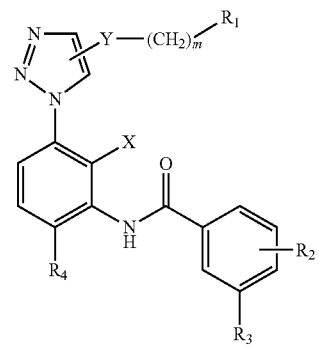

(I)

In some embodiments, X is hydrogen, methyl, methoxy or halogen groups;

In some embodiments, Y is —CH2-, —O—, —S—, —CO—, —CH2O—, —NR5-, —CONR6- or —NR7CO—, wherein, R5, R6 and R7 are independently hydrogen, C1-C4 alkyl, C1-C4 substituted alkyl, phenyl or substituted phenyl, substituted groups are halogen, C1-C4 alkyl, C1-C4 alkoxy, amino, hydroxy, decyl, carboxy, cyano, trifluoromethyl or imidazolyl groups;

In some embodiments, m is 0-6;

In some embodiments, R1 is hydrogen, amino, hydroxy, decyl, carboxy, cyano, —CONH2, C1-C4 alkyl, C1-C4 alkoxy, phenyl, substituted phenyl, substituted or unsubstituted nitrogen containing or oxygen containing 3-7 membered heterocyclic, —NR8COR9, —CONR10R11 or —NR10R11 groups, wherein R8 is hydrogen, C1-C4 alkyl, C1-C4 haloalkyl, phenyl or substituted phenyl, R9 is amino, hydroxyl, C1-C4 alkyl, C1-C4 alkoxy, phenyl or substituted phenyl, substituted or unsubstituted nitrogen containing or oxygen containing 3-7 membered heterocyclic, R10 and R11 independently represent hydrogen, C1-C4 alkyl, phenyl or substituted phenyl, substituted or unsubstituted nitrogen containing or oxygen containing 3-7 membered heterocyclic groups or nitrogen or oxygen containing 3-7 membered heterocyclic ring formed by linking R10 and R11, the said substitution groups are halogen, C1-C4 alkyl, C1-C4 alkoxy, amino, hydroxy, decyl, carboxy, cyano, trifluoromethyl or imidazolyl groups;

In some embodiments, R2 represents disubstituted or trisubstituted halogen, C1-C4 alkyl, C1-C4 alkoxy, trifluoromethyl, nitro or cyano;

In some embodiments, R3 represents amino, methylamino, aminomethyl, hydroxy, hydroxymethyl, decyl or —CONH2;

In some embodiments, R4 represents N-methylpiperazine, 1,2-dimethyl piperazine or N-methylhomopiperazine.

In some embodiments, X is preferentially hydrogen, fluorine, chlorine or alkyl groups.

In some embodiments, Y is preferentially —NR5-, CONR6- or —NR7CO—; R5, R6 and R7 are independently hydrogen, alkyl, ethyl, propyl, cyclopropyl or isopropyl groups.

In some embodiments, Y is also preferentially —NR5-, —CONR6- or —NR7CO—; R5, R6 and R7 are independently substituted phenyl group, wherein the substitutions are methyl, ethyl, isopropyl, tert-butyl, cyclopropyl, methoxy, cyano, halogen, trifluoromethyl or imidazolyl.

In some embodiments, said substituted or unsubstituted nitrogen containing or oxygen containing 3-7 membered heterocyclic groups are preferentially azacyclopropyl, azacycline, tetrahydropyrrole, piperidine, cyclohexmide, lactam, tetrahydrofuran, tetrahydropyran, morpholine, 1,4-oxazinidine, hexahydropyridazine, imidazoline, imidazolium, piperazine, the substituent is halogen, methyl, ethyl, phenyl, hydroxy, amino, hydroxymethyl or aminomethyl.

In some embodiments, R1 preferentially represents —NR8COR9, —CONR10R11 or —NR10R11, while R8, R9, R10 and R11 represents C1-C4 alkyl groups.

In some embodiments, R2 preferentially represents tri-substitutions, where the substitutions are fluorine, chlorine, bromine, methyl, methoxy, nitro, trifluoromethyl or cyano groups.

The present disclosure also includes pharmaceutically acceptable salts of compound (I) and its solvates, which all have the same pharmacological functions as that of compound (I).

Another aspect of the present disclosure comprises a drug combination, which includes compound (I) or its pharmaceutically usable salts, or solvates, and one or more pharmaceutically usable carriers, diluents and excipients.

Another aspect of the present disclosure comprises applications of using compound (I) or its pharmaceutically usable salts or solvates to prepare drugs to treat diseases mediated by the enzyme through inhibiting MLL1-WDR5 protein-protein interaction, the said diseases are such as MLL gene fusion type leukemia that can be treated through inhibition of MLL1 enzymatic activities.

Dosage of the compound in this disclosure used clinically comprises 0.01 mg-1000 mg/day, which can deviate from the range according to severity of diseases or different formulation.

In some of the preferred applications, compounds based on compound (I) can contain sufficient basic groups to form salts. Representative salts include inorganic acid salts, organic acid salts, hydrobromide and sulfuric acid salts; pharmaceutical use organic salts, including acetate, trifluoroacetate, lactate, succinate, fumarate, maleate, citrate, methanesulfonate, p-benzoate and p-toluenesulfonate salts.

In the meantime, another aspect of the present disclosure comprises preparation methods of compounds related to compound (I), including the following steps:

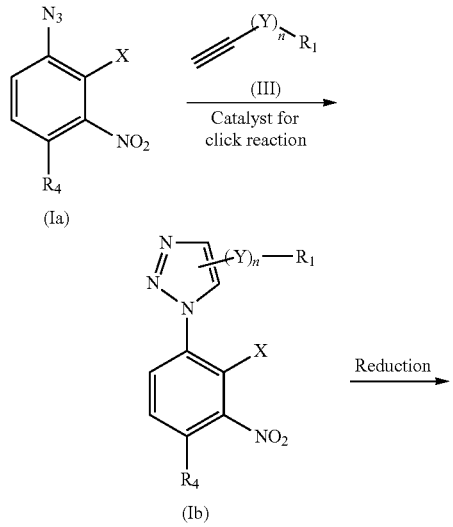

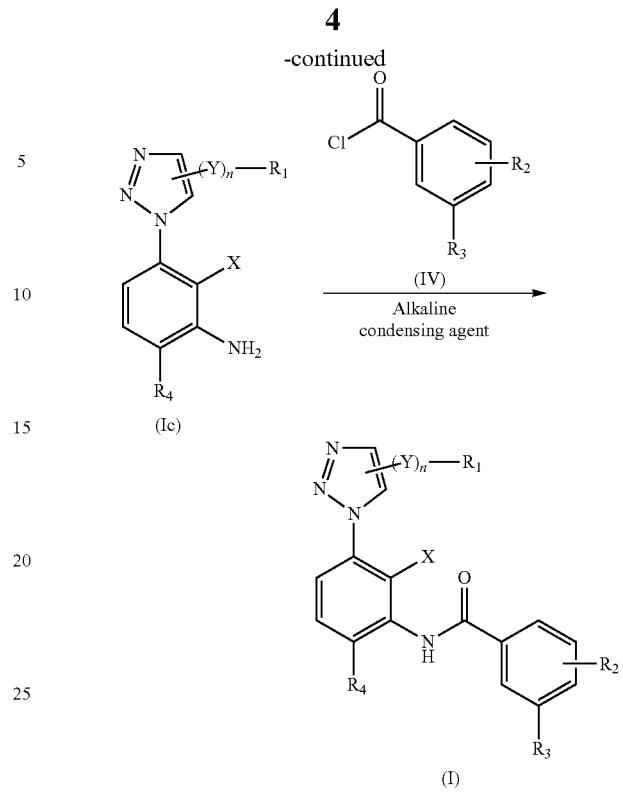

In some embodiments, R1, R2, R3, R4, X, Y and n are as defined previously;

In some embodiments, the intermediate Ia can be obtained through the following synthesis route,

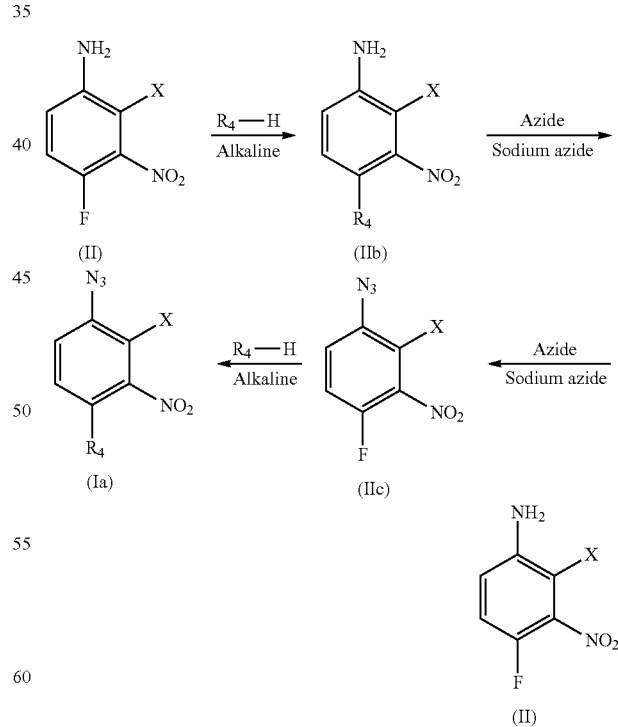

The following are some of the pharmacodynamic tests and results of the compound in the present disclosure:

MLL1 enzymatic activities are determined by MLL1 and WDR5 protein-protein interactions; MLL1 enzymatic activities affect the acetylation levels of H3K4. The H3K4 acetylation levels increase abnormally in MLL fusion type leukemia, while the downstream Hox and Meis-1 gene expression levels increase abnormally. When MLL1-WDR5 protein-protein interactions are inhibited, MLL1 catalytic activities decrease, H3K4 acetylation levels decrease, Hox and Meis-1 expression levels decrease, (which) inhibit leukemia cell proliferation.

Biphenyl compound DDO-2084 was already reported to be able to inhibit MLL1-WDR5 protein-protein interactions, lower MLL1 catalytic activities, downregulate small molecule inhibitor expressions from Hox and Meis-1 genes (Eur. J. Med. Chem. 2016, 124, 480-489), wherein DDO-2084 was the compound used as positive control.

TABLE 1

Inhibition activities of the compounds in this present disclosure over MLL1-WDR5 protein-protein interactions and related biological activities

| Compound numbering in application Examples[a] | MLL1-WDR5 PPI inhibition activity (nM) | Inhibition on H3K4 acetylation level | Downregulation of Hox and Meis-1 expression |
|---|---|---|---|
| 1 | <80 | Yes | Yes |
| 2 | <50 | Yes | Yes |
| 3 | <10 | Yes | Yes |
| 4 | <10 | Yes | Yes |
| 5 | <10 | Yes | Yes |
| 6 | <10 | Yes | Yes |
| 7 | <10 | Yes | Yes |
| 8 | <10 | Yes | Yes |
| 9 | <50 | Yes | Yes |
| 10 | <10 | Yes | Yes |
| 12 | <80 | Yes | Yes |
| 13 | <80 | Yes | Yes |
| 14 | <10 | Yes | Yes |
| 15 | <10 | Yes | Yes |
| 16 | <10 | Yes | Yes |
| 17 | <50 | Yes | Yes |
| 18 | <50 | Yes | Yes |
| 19 | <50 | Yes | Yes |
| 21 | <80 | Yes | Yes |
| 22 | <10 | Yes | Yes |
| 23 | <50 | Yes | Yes |
| 24 | <50 | Yes | Yes |
| 25 | <50 | Yes | Yes |
| DDO-2084[b] | 88.7 ± 4.9 | Yes | Yes |

[a]Refer to application Examples for specific compound structures;
[b]Structure of DDO-2084:

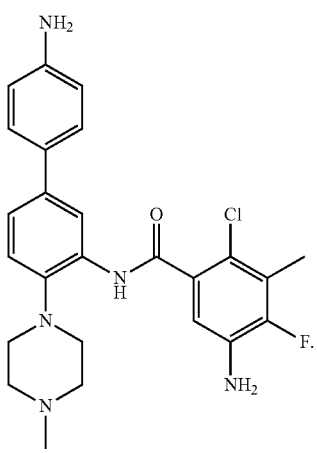 [SMILES: Cc1c(F)c(N)cc(C(=O)Nc2cc(-c3ccc(N)cc3)ccc2N2CCN(C)CC2)c1Cl]

As shown in Table 1, the compounds in this present disclosure have relatively strong inhibitory activities on MLL1-WDR5 protein-protein interactions.

In the meantime, RT-PCR experiments at cellular level were conducted with some of the compounds in the present disclosure, with results listed in Table 1 on whether some of the compounds inhibited downstream Hox and Meis-1 gene expression levels. Results showed that all compounds in the present disclosure with inhibitory activities on MLL1-WDR5 protein-protein interactions can all inhibit downstream Hox and Meis-1 gene expressions. Inhibition results at the cellular levels of some of the compounds on the downstream Hox and Meis-1 expression levels were plotted in FIG. 1, wherein FIG. 1 showed, the inhibition level of the compound in application Example 7 at 2.5 μM reached the same level as that of the positive control DDO-2084 at 5 μM, while the effects of that from the application Example 7 were better than that of DDO-2084 at the same 5 μM.

In addition, Western-blot experiments at cellular level were conducted with some of the compounds in the present disclosure, with results listed in Table 1 on whether some of the compounds in the present disclosure inhibited H3K4 acetylation levels. Results showed that all compounds in the present disclosure with inhibitory activities on MLL1-WDR5 protein-protein interactions all downregulated H3K4 acetylation levels. The inhibition on MLL1 catalytic activities at the cellular level for some of the compounds was plotted in FIG. 2. As FIG. 2 shows, application Example 7 can inhibit MLL1 catalytic activities in a dose-dependent manner to reduce the expression levels of H3K4me1/2/3, and it is showed that the results from application Example 7 was better than that of DDO-2084 at the same 10 μM concentration.

In addition, published paper (Eur. J. Med. Chem. 2016, 124, 480-489. Referred to as "Paper 1" below) has reported series of biphenyl inhibitors on MLL1-WDR5 protein-protein interactions, with structures of:

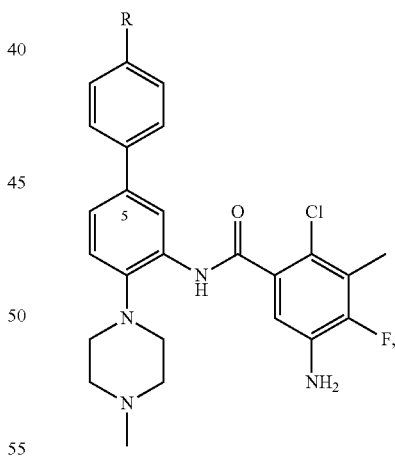

while the compounds in this present disclosure differ from them by changing the structures on how the two benzene rings are linked, wherein position 5 is linked by triazole groups, such changes increased the water solubility significantly of the compounds in this present disclosure, reduced the toxicity of the compounds but retained the original MLL1-WDR5 inhibitory activities. We have chosen some of the biphenyl compounds from Paper 1 and some of the un-reported biphenyl compounds for solubility and toxicity tests using the same testing methods in this present disclosure, and the results are below:

TABLE 2

Comparison of target activity and solubility of some of the compounds in this present disclosure (Examples) and some of the compounds in Paper 1

| Compound number and structure of this present disclosure | MLL1-WDR5 PP1 inhibition activity (nM) | Solubility (pH = 7.4) μg/mL | Structures of some compounds from publication (Eur. J. Med. Chem. 2016, 124, 480-489.) | MLL1-WDR5 PP1 inhibition activity (nM) | Solubility (pH = 7.4) μg/mL |
|---|---|---|---|---|---|
| 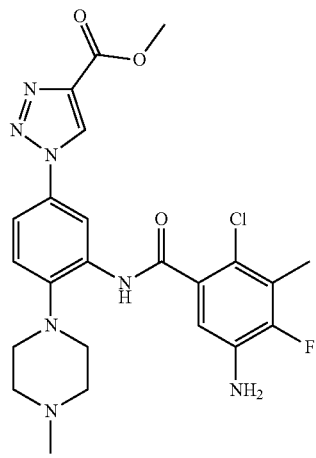 [SMILES: COC(=O)c1cn(-c2ccc(N3CCN(C)CC3)c(NC(=O)c3cc(N)c(F)c(C)c3Cl)c2)nn1] Example 1 | 67.8 | 20 | 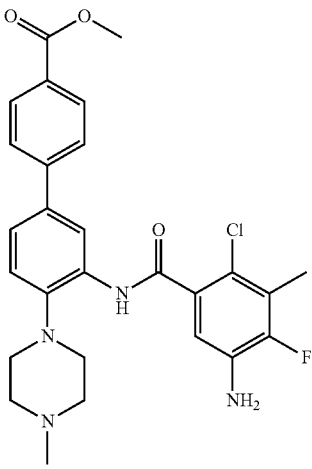 [SMILES: COC(=O)c1ccc(-c2ccc(N3CCN(C)CC3)c(NC(=O)c3cc(N)c(F)c(C)c3Cl)c2)cc1] | 70.0 | 1.9 |
| 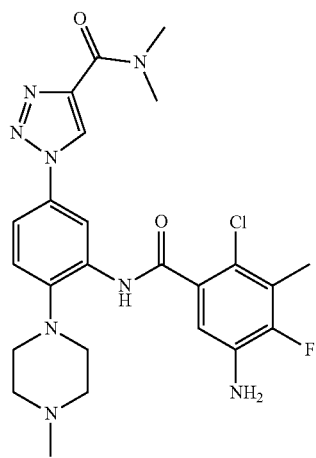 [SMILES: Cc1c(F)c(N)cc(C(=O)Nc2cc(-n3cc(C(=O)N(C)C)nn3)ccc2N2CCN(C)CC2)c1Cl] Example 3 | 33.9 | 170 | 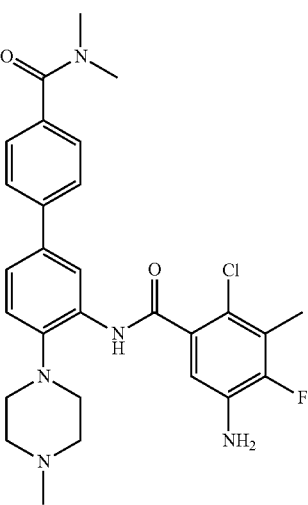 [SMILES: Cc1c(F)c(N)cc(C(=O)Nc2cc(-c3ccc(C(=O)N(C)C)cc3)ccc2N2CCN(C)CC2)c1Cl] | 73.0 | 21 |

TABLE 2-continued

Comparison of target activity and solubility of some of the compounds in this present disclosure (Examples) and some of the compounds in Paper 1

| Compound number and structure of this present disclosure | MLL1-WDR5 PP1 inhibition activity (nM) | Solubility (pH = 7.4) μg/mL | Structures of some compounds from publication (Eur. J. Med. Chem. 2016, 124, 480-489.) | MLL1-WDR5 PP1 inhibition activity (nM) | Solubility (pH = 7.4) μg/mL |
|---|---|---|---|---|---|
| Example 4 | 11.2 | 200 | | 55.6 | 27 |
| Example 11 | 65.7 | 30 | | 47.9 | 3.1 |
| Example 13 | 90.3 | 110 | | 88.7 | 9.5 |

TABLE 2-continued

Comparison of target activity and solubility of some of the compounds in this present disclosure (Examples) and some of the compounds in Paper 1

| Compound number and structure of this present disclosure | MLL1-WDR5 PP1 inhibition activity (nM) | Solubility (pH = 7.4) μg/mL | Structures of some compounds from publication (Eur. J. Med. Chem. 2016, 124, 480-489.) | MLL1-WDR5 PP1 inhibition activity (nM) | Solubility (pH = 7.4) μg/mL |
| --- | --- | --- | --- | --- | --- |
| 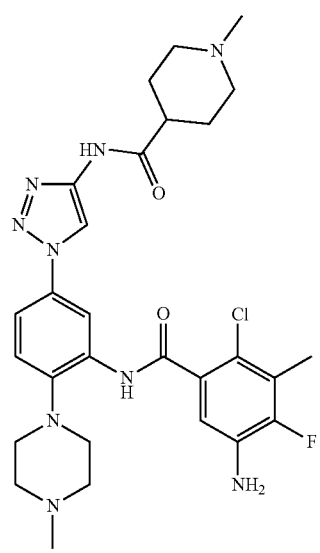 [SMILES: Cc1c(F)c(N)cc(C(=O)Nc2cc(-n3cc(NC(=O)C4CCN(C)CC4)nn3)ccc2N2CCN(C)CC2)c1Cl]<br>Example 14 | 6.0 | 630 | 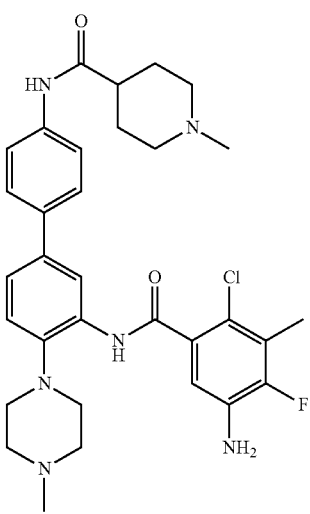 [SMILES: Cc1c(F)c(N)cc(C(=O)Nc2cc(-c3ccc(NC(=O)C4CCN(C)CC4)cc3)ccc2N2CCN(C)CC2)c1Cl] | 6.5 | 54 |
| 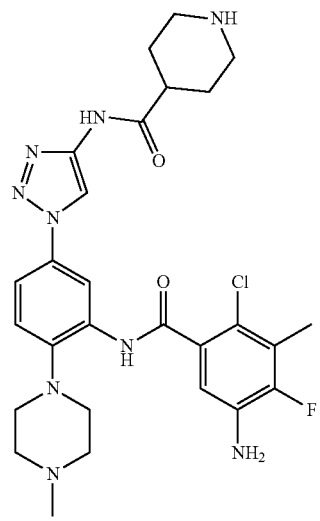 [SMILES: Cc1c(F)c(N)cc(C(=O)Nc2cc(-n3cc(NC(=O)C4CCNCC4)nn3)ccc2N2CCN(C)CC2)c1Cl]<br>Example 15 | 12.3 | 1235 | 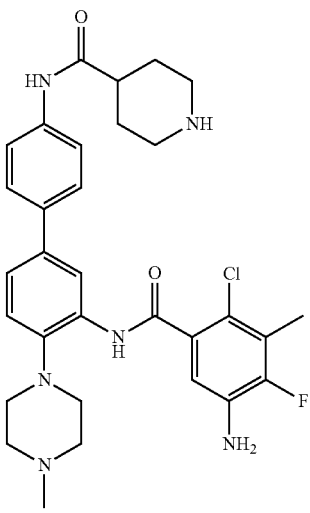 [SMILES: Cc1c(F)c(N)cc(C(=O)Nc2cc(-c3ccc(NC(=O)C4CCNCC4)cc3)ccc2N2CCN(C)CC2)c1Cl] | 8.5 | 125 |

TABLE 2-continued

Comparison of target activity and solubility of some of the compounds in this present disclosure (Examples) and some of the compounds in Paper 1

| Compound number and structure of this present disclosure | MLL1-WDR5 PP1 inhibition activity (nM) | Solubility (pH = 7.4) µg/mL | Structures of some compounds from publication (Eur. J. Med. Chem. 2016, 124, 480-489.) | MLL1-WDR5 PP1 inhibition activity (nM) | Solubility (pH = 7.4) µg/mL |
|---|---|---|---|---|---|
| | 6.7 | 1303 | | 7.6 | 110 |

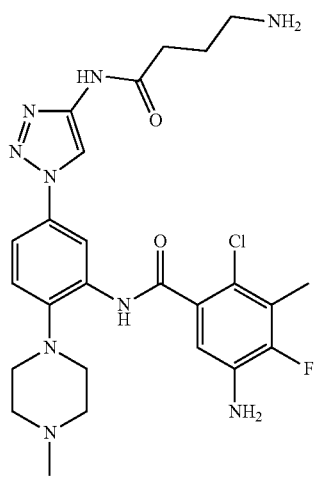 [SMILES: Cc1c(F)c(N)cc(C(=O)Nc2cc(-n3cc(NC(=O)CCCN)nn3)ccc2N2CCN(C)CC2)c1Cl]

Example 16

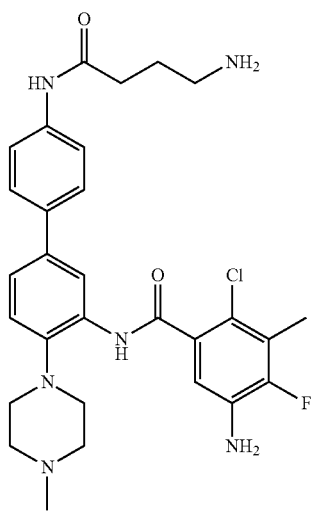 [SMILES: Cc1c(F)c(N)cc(C(=O)Nc2cc(-c3ccc(NC(=O)CCCN)cc3)ccc2N2CCN(C)CC2)c1Cl]

It is noted from the comparison of data in Table 2 for the compounds that, when the other groups remained the same, replacement of the benzene rings by triazole groups in this present disclosure retained targeting activity and improve water solubility significantly.

In the meantime, subacute toxicity experiments were conducted to evaluate the safety of some of the compounds in the present disclosure in mouse. Some of the triazole compounds from this present disclosure (application Examples 4, 6, 7, 16 and 22) and compounds DDO-2113 and DDO-2117 from Paper 1 were given by intraperitoneal injection at 80 mg/kg to female balb/c mice, 6 mice per group, for 10 consecutive days to observe mouse survival and average body weight changes. As shown in FIG. 3, there were no death after dosing for 10 days for some of the compounds from this present disclosure (application Examples 4, 6, 7, 16 and 22) with slight body weight increase, while after dosing with the compounds DDO-2113 and DDO-2117 from the paper (Eur. J. Med. Chem. 2016, 124, 480-489), all mice died after dosing for 5 days with DDO-2113 at 80 mg/kg and those given DOO-2117 had apparent body weight decrease. The comparison of post dosing survival and average body weight changes, that no death after dosing for 10 days with the triazole compounds in this present disclosure with slight body weight increase in contrast to that with deaths and body weight decreases after dosing with diphenyl series compounds of DDO-2113 and DDO-2117, indicates the very good dosing safety of the phenyltriazoles in this present disclosure.

Wherein, DDO-2113 and DDO-2117 are compounds from Paper 1 with the structures:

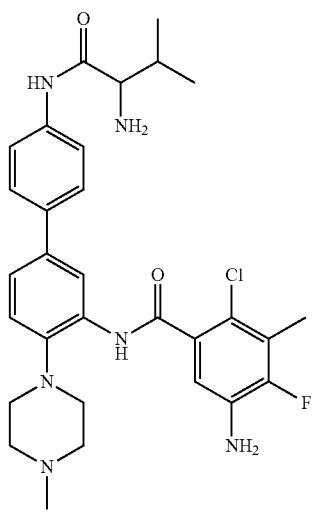

DOO-2113

-continued

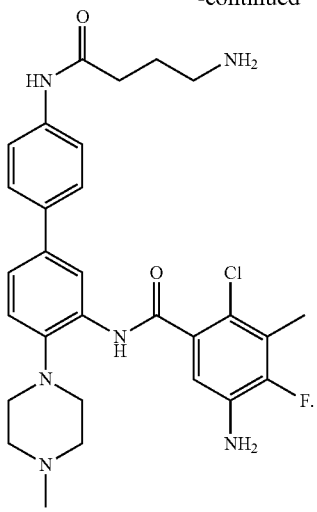

DOO-2117

Anti-proliferation experiments were conducted with leukemia cells with some of the compounds in the present disclosure. Table 3 listed the results of evaluation of the anti-proliferation activities for some of the compounds from this present disclosure conducted with acute leukemia cells, wherein MV4-11 is human acute leukemia monocyte, Molm-13 is human acute myeloid leukemia cells, and K562 is human chronic myeloid leukemia cells. Table 3 indicated that the compounds in this present disclosure have very good inhibition activity of different kinds of leukemia cells.

TABLE 3

Anti-proliferation activities of some of the compounds in this present disclosure on leukemia cells

| Compound numbers in the application Examples[a] | $GI_{50}/\mu M$ (MV-411) | $GI_{50}/\mu M$ (Molm-13) | $GI_{50}/\mu M$ (K562) |
|---|---|---|---|
| 1 | 8.9 ± 0.3 | 11.8 ± 0.9 | ND |
| 3 | 44.6 ± 1.3 | 22.8 ± 5.5 | >100 |
| 4 | 10.5 ± 2.0 | ND[b] | 34.4 ± 0.9 |
| 5 | 15.1 ± 1.2 | 13.0 ± 0.6 | 27.5 ± 2.8 |
| 6 | 10.9 ± 0.2 | 8.2 ± 0.6 | 10.4 ± 0.7 |
| 7 | 8.0 ± 1.2 | 9.9 ± 1.9 | 12.9 ± 0.4 |
| 8 | 17.8 ± 3.6 | 11.9 ± 1.5 | 34.1 ± 1.2 |
| 9 | 27.4 ± 2.1 | ND[b] | 35.8 ± 2.7 |
| 10 | 13.5 ± 1.2 | 13.5 ± 1.2 | 13.5 ± 1.2 |
| 11 | 13.5 ± 1.5 | 13.5 ± 1.5 | 13.5 ± 1.5 |
| 12 | 23.2 ± 3.2 | ND[b] | ND[b] |
| 13 | 10.1 ± 1.3 | 9.2 ± 1.4 | 10.5 ± 2.0 |
| 14 | 9.5 ± 1.0 | 11.0 ± 2.0 | 14.1 ± 1.3 |
| 15 | 14.3 ± 1.7 | 18.5 ± 1.9 | 12.9 ± 0.2 |
| 16 | 15.1 ± 0.9 | ND[b] | 15.0 ± 0.8 |
| 17 | 10.4 ± 1.1 | 7.3 ± 0.8 | 21.3 ± 2.4 |
| 18 | 11.2 ± 1.3 | 15.4 ± 2.2 | ND[b] |
| 19 | 13.7 ± 1.4 | 16.8 ± 2.0 | 13.5 ± 1.2 |
| 20 | 8.6 ± 0.6 | 10.1 ± 1.3 | 10.5 ± 2.0 |
| 21 | 12.7 ± 0.8 | 7.7 ± 0.9 | 10.5 ± 0.8 |
| 22 | 9.5 ± 0.4 | 11.2 ± 0.8 | 10.9 ± 0.7 |
| 23 | ND[b] | 17.9 ± 1.6 | 27.7 ± 0.3 |
| 24 | 11.3 ± 0.7 | 12.9 ± 0.9 | 13.5 ± 2.2 |
| 25 | 10.9 ± 0.9 | 8.5 ± 0.7 | 11.3 ± 0.7 |
| DDO-2084 | 17.7 ± 2.3 | ND[b] | 50.5 ± 5.5 |

[a]Refer to the application Examples for the chemical structures;
[b]ND indicates not tested;

The phenyl triazole compounds in this have relatively strong inhibition activity on MLL1-WDR5 protein-protein interactions, lowering the MLL1 catalytic activities of MLL1 at the cellular level, down regulating the gene expression levels of Hox and Meis-1 and induce apoptosis of leukemia cells, and that the phenyl triazole compounds in this present disclosure have shown very good water solubility and pharmaceutical safety, and can be used for treating leukemia.

EXAMPLE 1

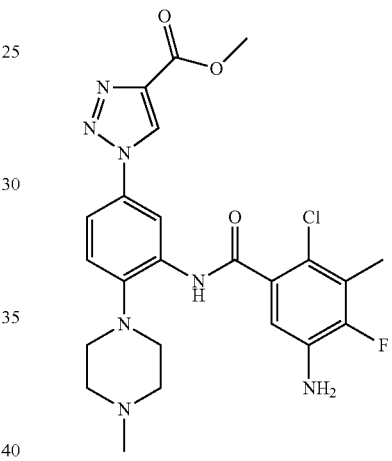

Figure 1:
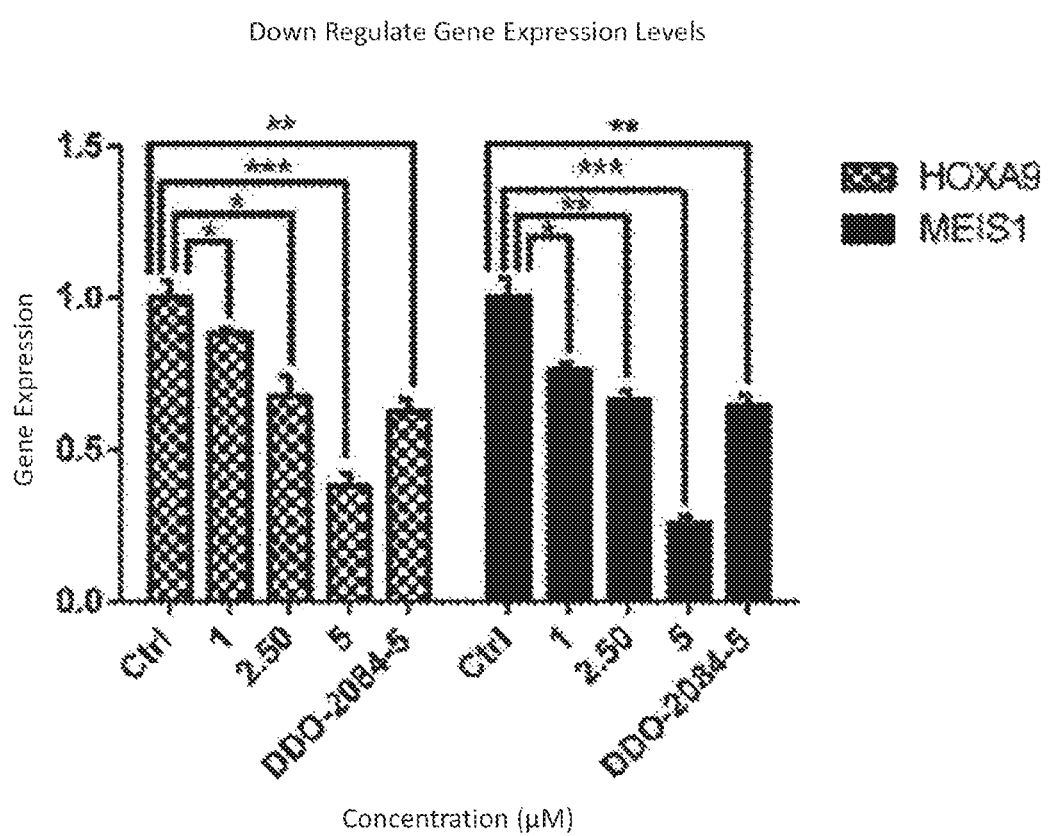
FIG. 1 is the RT-PCR experiment for application Example 7 to show the lowered Hoxa9 and Meis-1 gene expressions in cells
Figure 2:
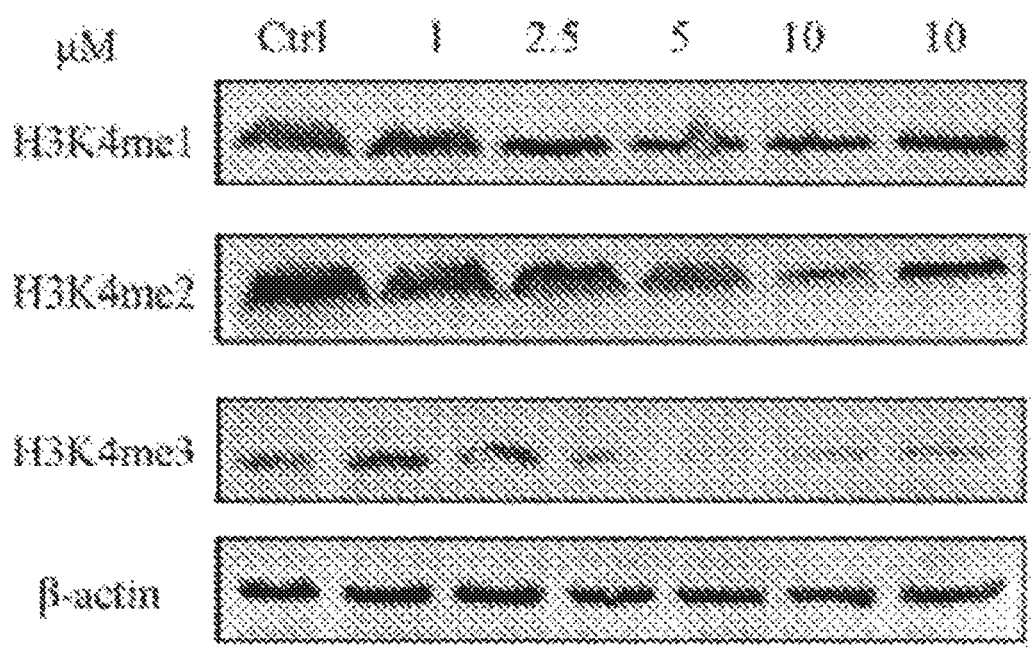
FIG. 2 is the Western Blot experiment for application Example 7 to show the effects on MLL1 enzymatic activity in cells.
Figure 3:
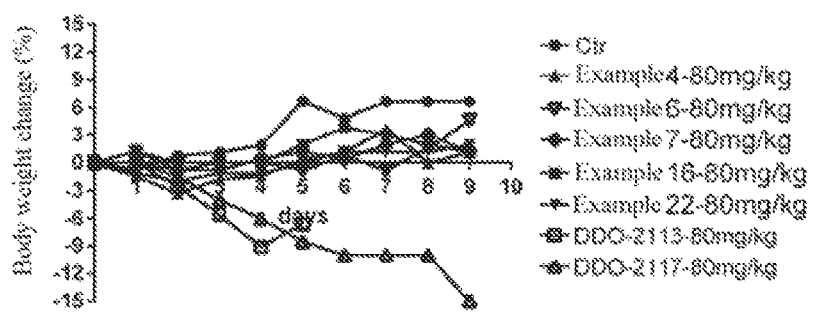
FIG. 3 is the toxicity comparison of the compounds in this present disclosure to some of the compounds on Article 1

1-(3-(5-amino-2-chloro-4-fluoro-3-methyl benzoylamino)-4-(4-methyl piperazine-1-group)phenyl)-1H-1,2,3-methyl triazole-4-carboxylate Preparation of 4-(4-methylpiperazin-1-group)-3-nitroaniline (IIb)

Dissolve 4-fluoro-3-nitroaniline (II) (6 g, 38.4 mmol) in 50 mL acetonitrile, add N-methylpiperazin (5.8 g, 6.3 mL, 57.6 mmol) and N, N-diisopropylethylamine (9.5 mL, 57.6 mmol), and heat and reflux for 12 h. The crude is obtained after spin dry and purified by silica gel column chromatography (dichloromethane:methanol=20:1) to obtain red-brown solid (8.9 g, 97.8%). $^1$H NMR (300 MHz, DMSO-d$_6$) δ7.06 (d, J=8.6 Hz, 1H), 6.76 (s, 1H), 6.69 (d, J=8.5 Hz, 1H), 5.34 (s, 2H), 2.70 (t, J=4.4 Hz, 4H), 2.27 (br s, 4H), 2.09 (s, 3H). m/z (EI-MS); 259.1 [M+Na]$^+$.

Preparation of 1-(4-azido-2-nitrophenyl)-4-methylpiperazine (Ia)

Dissolve 4-(4-methylpiperazin-1-group)-3-nitroaniline (IIb)(4.0 g, 17.0 mmol) in 100 mL 2M/HCl, reduce the temperature to 0° C., add 10 mL of sodium nitrite (1.76 g, 25.5 mmol) water solution dropwise, stir for 30 min at 0° C., add 10 mL sodium azide (2.2 g, 34.0 mmol) water solution dropwise, stir 30 min at 0° C. and then stir 2 h at room temperature. The product is precipitated with 2M/NaOH at pH=9-10, vacuum filter and heat dry to obtain red-brown solid (4.0 g, 91.3%). $^1$H NMR (300 MHz, DMSO-$d_6$) δ7.48 (d, J=2.2 Hz, 1H), 7.34-7.20 (m, 2H), 2.85 (t, J=4.7 Hz, 4H), 2.31 (t, J=4.8 Hz, 4H), 2.11 (s, 3H). m/z (EI-MS): 261.1 [M+H]$^-$.

Preparation of 1-(4-(4-methylpiperazin-1-group)-3-nitrophenyl)-1H-1,2,3,-triazole-4-methyl carboxylate (Ib)

Dissolve 1-(4-azido-nitrophenyl)-4-methylpiperazine (Ia) (1.0 g, 3.8 mmol) in 50 mL methanol, add methyl propiolate (0.96 g, 11.4 mmol), cuprous iodide (0.07 g, 0.38 mmol), N,N-diisopropylethylamine (0.12 mL, 0.76 mmol), heat reflux for 48 h, filter, concentrate, and beat up with ethyl acetate to obtain red-brown solid (0.8 g, 61.5%). $^1$H NMR (300 MHz, DMSO-$d_6$) δ9.45 (s, 1H), 8.36 (d, J=2.7 Hz, 1H), 8.11-8.01 (m, 1H), 7.42 (d, J=9.1 Hz, 1H), 3.80 (s, 3H), 2.99 (t, J=5.4 Hz, 4H), 2.35 (t, J=5.2 Hz, 4H), 2.13 (s, 3H). m/z (EI-MS); 369.2 [M+Na]$^+$.

Preparation of 1-(3-amino-4-(4-methylpiperazin-1-group)phenyl-1H-1,2,3-methyl triazole-4-methyl carboxylate (Ic)

Dissolve 1-(4-(4-methylpiperazin-1-group)-3-nitrophenyl)-1H-1,2,3-methyl triazole-4-methyl carboxylate (Ib) (3.8 g, 12.0 mmol) in 50 mL methanol, add Pd/C of catalytic amount, pump in hydrogen, stir at room temperature for 7 h, concentrate by vacuum filtering to obtain pink solid (3.0 g, 78.9%). $^1$H NMR (300 MHz, DMSO-$d_6$) δ9.28 (s, 1H), 7.28 (d, J=1.9 Hz, 1H), 7.07 (d, J=1.9 Hz, 2H), 5.15 (s, 2H), 3.90 (s, 3H), 2.87 (t, J=4.5 Hz, 4H), 2.53 (br s, 4H), 2.26 (s, 3H). m/z (ESI-MS): 317.1763 [M+H]$^+$.

Preparation of 1-(3-(5-Amino-2-chloro-4-fluoro-3-methylbenzoylamino)-4-(4-methylpiperazin-1-group)phenyl)-TH-1, Methyl 2,3-triazole-4-carboxylate (1)

Dissolve 1-(3-amino-4-(4-methylpiperazin-1-group)phenyl-1H-1,2,3-triazole-4-methyl carboxylate (Ic) (1.7 g, 5.3 mmol) in 100 mL anhydrous dichloromethane, add pyridine (0.43 mL, 5.3 mmol), add 20 mL dichloromethane solution of 2-chloro-3-methyl-4-fluoro-5-nitrobenzoyl chloride (1.6 g, 6.4 mmol) drop wise in ice-water bath, stir 2 h at room temperature, filter under vacuum and heat dry to obtain light yellow solid; dissolve the light yellow (2.6 g, 4.9 mmol) in ethyl acetate, add stannous chloride (5.5 g, 24.4 mmol), heat and reflux for 3 h before cooling down to room temperature, dilute with 100 mL ethyl acetate, neutralize with saturated sodium bicarbonate till no additional white gel-like precipitating out, filter under vacuum, wash the filter cake with ethyl acetate till no ultraviolet absorption, extract the filtrate with ethyl acetate till no ultraviolet absorption, combine the organic phases, dry with anhydrous sodium sulfate, concentrate to obtain the crude product, beat up with ethyl acetate, filter under vacuum to obtain gray-white solid 1 (2.3 g, 93.9%). $^1$H NMR (300 MHz, DMSO-$d_6$) δ9.52-9.45 (m, 2H), 8.69 (s, 1H), 7.73 (dd, J=8.7, 2.7 Hz, 1H), 7.46 (d, J=8.6 Hz, 1H), 6.92 (d, J=9.2 Hz, 1H), 5.53 (s, 2H), 3.92 (s, 3H), 3.00-2.90 (m, 4H), 2.51 (br s, 4H), 2.28 (d, J=2.6 Hz, 3H), 2.24 (s, 3H). (EI-MS): 502.9 [M+H]$^+$.

EXAMPLE 2

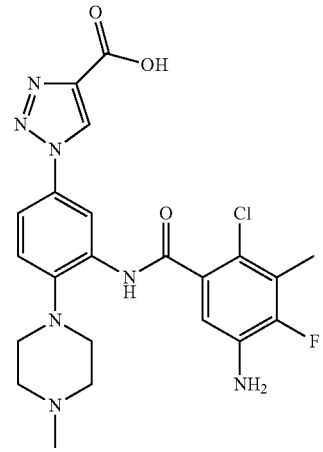 [SMILES: Cc1c(F)c(N)cc(C(=O)Nc2cc(-n3cc(C(=O)O)nn3)ccc2N2CCN(C)CC2)c1Cl]

Preparation of 1-(3-(5-Amino-2-chloro-3-methyl-benzoylamino)-4-(4-methylpiperazin-1-group)phenyl)-1H-1,2,3-Triazole-4-carboxylic acid (2)

Dissolve 1-(3-(5-Amino-2-chloro-3-methylbenzoylamino)-4-(4-methylpiperazin-1-yl)phenyl)-1H-1,2,3-triazole-4-Methyl formate (1) (2.3 g, 4.6 mmol) in THF, add lithium hydroxide solution (1M, 15 mL), stir for 8 h at room temperature, rotate dry to remove THF followed by acidification using 2M chloric acid to obtain white solid (1.7 g, 80.4%). $^1$H NMR (300 MHz, DMSO-$d_6$) δ9.52-9.45 (m, 2H), 8.69 (s, 1H), 7.73 (dd, J=8.7, 2.7 Hz, 1H), 7.46 (d, J=8.6 Hz, 1H), 6.92 (d, J=9.2 Hz, 1H), 5.53 (s, 2H), 3.92 (s, 3H), 3.00-2.90 (m, 4H), 2.50 (br s, 4H), 2.28 (d, J=2.6 Hz, 3H), 2.24 (s, 3H). (EI-MS): 488.9 [M+H]$^+$.

EXAMPLE 3

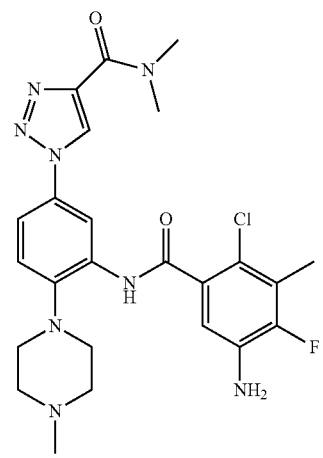 [SMILES: Cc1c(F)c(N)cc(C(=O)Nc2cc(-n3cc(C(=O)N(C)C)nn3)ccc2N2CCN(C)CC2)c1Cl]

Preparation of 1-(3-(5-Amino-2-chloro-4-fluoro-3-methylbenzoylamino)-4-(4-methylpiperazin-1-group)phenyl)-N, N-dimethyl-1H-1,2,3 triazole-4-carboxamide (3)

Dissolve 1-(3-(5-Amino-2-chloro-4-fluoro-3-methylbenzoylamino)-4-(4-methylpiperazin-1-group)phenyl)-1H-1,2,3-Triazole-4-carboxylic acid (2) (0.18 g, 0.36 mmol) in 10 mL DMF, add BOP (0.32 g, 0.72 mmol), trimethylamine (0.10 mL, 0.72 mmol) and dimethylamino hydrochloride (58.7 mg, 0.72 mmol), stir for 4 h at room temperature. Dilute the reaction mixture with 50 mL ethyl acetate, remove DMF with saturated sodium chloride, dry the organic phase with anhydrous sodium sulphate, dry out the organic solvent with rotations to obtain raw product, isolate and purify with silica gel column chromatography (Dichloromethane:methanol=50:1) to obtain gray white solid. The yield is 78.4%. $^1$H NMR (300 MHz, DMSO-$d_6$) δ9.59 (s, 1H), 9.18 (s, 1H), 8.63 (d, J=2.5 Hz, 1H), 7.71 (dd, J=8.6, 2.6 Hz, 1H), 7.42 (d, J=8.6 Hz, 1H), 6.83 (d, J=9.2 Hz, 1H), 5.50 (s, 2H), 3.11 (br s, 10H), 3.02 (s, 3H), 2.70-2.69 (m, 4H), 2.24 (d, J=2.5 Hz, 3H). (EI-MS): 515.9 [M+H]$^+$.

EXAMPLE 4

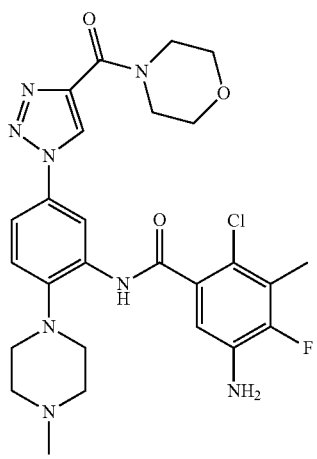 [SMILES: Cc1c(F)c(N)cc(C(=O)Nc2cc(-n3cc(C(=O)N4CCOCC4)nn3)ccc2N2CCN(C)CC2)c1Cl]

Preparation of 5-amino-2-chloro-4-fluoro-3-methyl-N-(2-(4-methylpiperazin-1-group)-5-(4-((morpholine-4-carbonyl)-1H-1,2,3-triazol-1-yl)phenyl)benzamide (4)

Using the methods in application Example 3, replace dimethylamino hydrochloride by morpholine to obtain gray white solid. The yield is 67.5%. $^1$H NMR (300 MHz, DMSO-$d_6$) δ9.61 (s, 1H), 9.24 (s, 1H), 8.64 (d, J=2.5 Hz, 1H), 7.73 (dd, J=8.6, 2.6 Hz, 1H), 7.44 (d, J=8.6 Hz, 1H), 6.86 (d, J=9.2 Hz, 1H), 5.52 (s, 2H), 4.06 (s, 2H), 3.68 (s, 6H), 3.12 (br s, 8H), 2.69 (s, 3H), 2.26 (d, J=2.6 Hz, 3H). (EI-MS): 558.9 [M+H]$^+$.

EXAMPLE 5

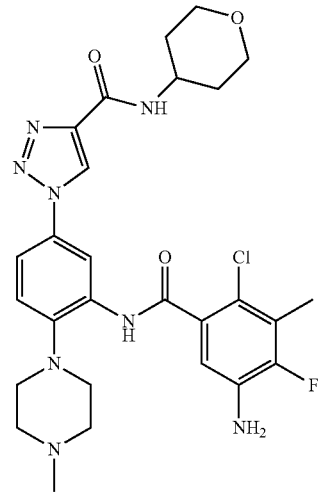 [SMILES: Cc1c(F)c(N)cc(C(=O)Nc2cc(-n3cc(C(=O)NC4CCOCC4)nn3)ccc2N2CCN(C)CC2)c1Cl]

Preparation of 1-(3-(5-Amino-2-chloro-4-fluoro-3-methylbenzoylamino)-4-(4-methylpiperazin-1-group)phenyl)-N-(tetrahydro-2H-pyran-4-yl)-1H-1,2,3-triazole-4-carboxamide Using the methods in application Example 3, replace dimethylamino hydrochloride with 4-aminotetrahydropyran to obtain gray white solid. The yield is 82.9%. $^1$H NMR (300 MHz, DMSO-$d_6$) δ9.52 (s, 1H), 9.26-9.24 (m, 1H), 8.65 (s, 2H), 7.71 (d, J=8.7 Hz, 1H), 7.42 (d, J=9.4 Hz, 1H), 6.89 (s, 1H), 5.53 (s, 2H), 4.06 (s, 1H), 3.9-3.86 (m, 2H), 2.99 (s, 6H), 2.71 (s, 4H), 2.38 (s, 3H), 2.25 (s, 3H), 1.71 (s, 4H). (EI-MS): 572.0 [M+H]$^+$.

EXAMPLE 6

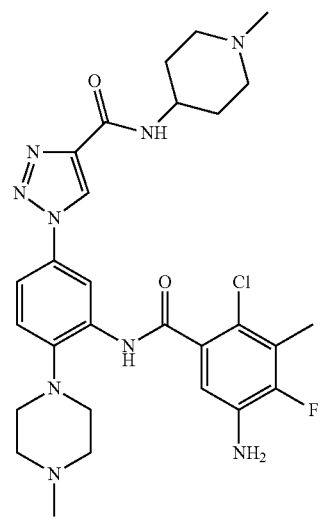 [SMILES: Cc1c(F)c(N)cc(C(=O)Nc2cc(-n3cc(C(=O)NC4CCN(C)CC4)nn3)ccc2N2CCN(C)CC2)c1Cl]

Preparation of 1-(3-(5-Amino-2-chloro-4-fluoro-3-methylbenzoylamino)-4-(4-methylpiperazin-1-group)phenyl)-N-(1-methylpiperidin-4-group)-1H-1,2,3-triazole-4-carboxamide Using the methods in application Example 3, replace dimethylamino hydrochloride with 4-amino-1-1methylpiperidin to obtain gray white solid. The yield is 49.9%. $^1$H NMR (300 MHz, DMSO-$d_6$) δ9.48 (s, 1H), 9.22 (s, 1H), 8.65 (d, J=2.6 Hz, 1H), 8.52 (d, J=8.2 Hz, 1H), 7.70 (dd, J=8.5, 2.7 Hz, 1H), 7.42 (d, J=8.6 Hz, 1H), 6.89 (d, J=9.2 Hz, 1H), 5.54 (s, 2H), 3.78 (s, 1H), 2.92 (t, J=4.6 Hz, 4H), 2.82-2.78 (m, 2H), 2.26 (d, J=2.7 Hz, 3H), 2.22 (s, 3H), 2.19 (s, 3H), 2.07-1.86 (m, 4H), 1.75-1.66 (m, 4H). (EI-MS): 585.0 [M+H]$^+$.

EXAMPLE 7

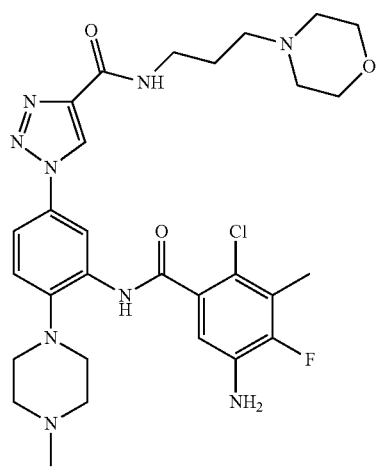 [SMILES: Cc1c(F)c(N)cc(C(=O)Nc2cc(-n3cc(C(=O)NCCCN4CCOCC4)nn3)ccc2N2CCN(C)CC2)c1Cl]

Preparation of 1-(3-(5-amino-2-chloro-4-fluoro-3-ethyl benzoylamino) 4-(4-methylpiperazin-1-group)-N-(3-morpholinopropyl)-1H-1,2,3-triazole-4-carboxamide (7)

Using the methods in application Example 3, replace dimethylamino hydrochloride with N-(3-aminopropyl)morpholine, and obtain gray-white solid. The yield is 94.2%. $^1$H NMR (300 MHz, DMSO-$d_6$) δ9.51 (s, 1H), 9.22 (s, 1H), 8.85 (t, J=5.8 Hz, 1H), 8.66 (s, 1H), 7.71 (dd, J=8.6, 2.7 Hz, 1H), 7.43 (d, J=8.8 Hz, 1H), 6.89 (d, J=9.2 Hz, 1H), 5.53 (s, 2H), 3.62 (t, J=4.6 Hz, 4H), 2.98-2.97 (m, 4H), 2.63 (s, 4H), 2.54 (s, 2H), 2.46-2.36 (m, 6H), 2.33 (s, 3H), 2.26 (d, J=2.6 Hz, 3H), 1.74-1.70 (m, 2H). (ESI-MS): 615.1 [M+H]$^+$.

EXAMPLE 8

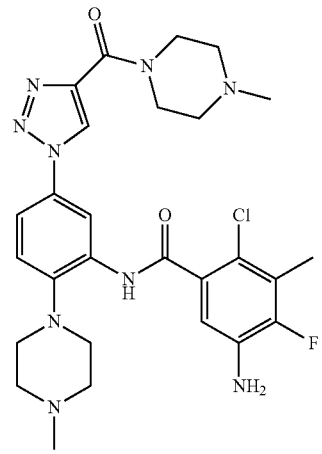 [SMILES: Cc1c(F)c(N)cc(C(=O)Nc2cc(-n3cc(C(=O)N4CCN(C)CC4)nn3)ccc2N2CCN(C)CC2)c1Cl]

Preparation of 5-amino-2-chloro-4-fluoro-3-ethyl-N-(2-(4-methylpiperazin-1-group)-5-(4-(methylpiperazin-1-Carbonyl)-1H-1,-1H-1,2,3-triazole-1-group)Phenyl)-carboxamide (8)

Using the methods in application Example 3, replace dimethylamino hydrochloride with N-methylpiperazin to obtain gray-white solid. The yield is 94.2%. $^1$H NMR (300 MHz, DMSO-$d_6$) δ9.51 (s, 1H), 9.22 (s, 1H), 8.85 (t, J=5.8 Hz, 1H), 8.66 (s, 1H), 7.71 (dd, J=8.6, 2.7 Hz, 1H), 7.43 (d, J=8.8 Hz, 1H), 6.89 (d, J=9.2 Hz, 1H), 5.53 (s, 2H), 3.62 (t, J=4.6 Hz, 4H), 2.98-2.97 (m, 4H), 2.63 (s, 4H), 2.54 (s, 2H), 2.46-2.36 (m, 6H), 2.33 (s, 3H), 2.26 (d, J=2.6 Hz, 3H), 1.74-1.70 (m, 2H). (ESI-MS): 571.0 [M+H]$^+$.

EXAMPLE 9

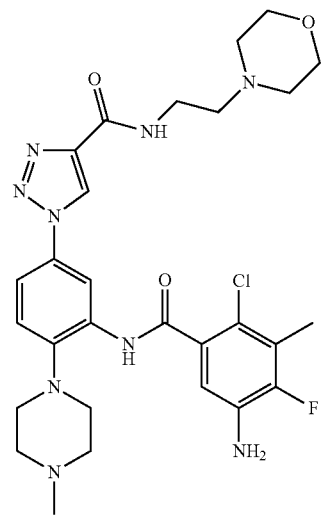 [SMILES: Cc1c(F)c(N)cc(C(=O)Nc2cc(-n3cc(C(=O)NCCN4CCOCC4)nn3)ccc2N2CCN(C)CC2)c1Cl]

Preparation of 1-(3-(5-amino-2-chloro-4-fluoro-3-ethyl benzoylamino)-4-(4-methylpiperazin-1-group) phenyl)-N-(2-Morpholine ethyl)-1H-1,2,3-triazole-4-carboxamide (9)

Using the methods in application Example 3, replace dimethylamino hydrochloride with N-Aminoethylmorpholine to obtain gray-white solid. The yield is 72.5%. $^1$H NMR (300 MHz, DMSO-d$_6$) δ9.51 (s, 1H), 8.66 (d, J=2.4 Hz, 1H), 8.56 (t, J=5.8 Hz, 1H), 7.71 (dd, J=8.7, 2.6 Hz, 1H), 7.43 (d, J=8.7 Hz, 1H), 6.89 (d, J=9.2 Hz, 1H), 5.54 (s, 2H), 3.58 (t, J=4.6 Hz, 4H), 3.44 (s, 2H), 2.96 (t, J=4.8 Hz, 4H), 2.59 (s, 4H), 2.54 (s, 2H), 2.44 (s, 4H), 2.30 (s, 3H), 2.26 (d, J=2.6 Hz, 3H). (ESI-MS): 601.0 [M+H]$^+$.

EXAMPLE 10

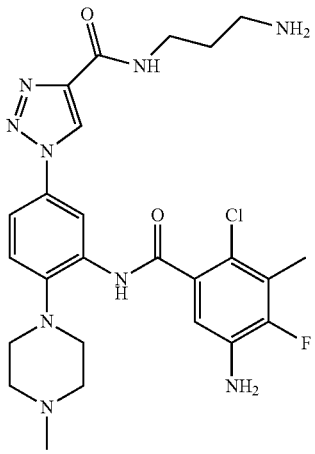 [SMILES: Cc1c(F)c(N)cc(C(=O)Nc2cc(-n3cc(C(=O)NCCCN)nn3)ccc2N2CCN(C)CC2)c1Cl]

Preparation of 1-(3-(5-amino-2-chloro-4-fluoro-3-ethyl benzoylamino)-4-(4-methylpiperazin-1-group) phenyl)-N-(3-aminopropyl)-1H-1,2,3-triazole-4-carboxamide (10)

Using the methods in application Example 3, replace dimethylamino hydrochloride with 1,3-propylene diamine to obtain gray-white solid. The yield is 64.5%. $^1$H NMR (300 MHz, DMSO-d$_6$) δ8.85 (s, 1H), 8.70 (s, 1H), 8.45 (d, J=2.1 Hz, 1H), 7.36 (dd, J=7.5, 2.0 Hz, 1H), 7.25 (s, 1H), 6.84 (d, J=7.5 Hz, 1H), 6.78 (d, J=5.7 Hz, 1H), 4.13 (s, 2H), 3.25-3.19 (m, 6H), 2.98 (t, J=4.9 Hz, 4H), 2.67-2.58 (m, 5H), 2.39 (s, 3H), 2.19-2.13 (m, 2H), 1.14 (s, 2H). (ESI-MS): 545.0 [M+H]$^+$.

EXAMPLE 11

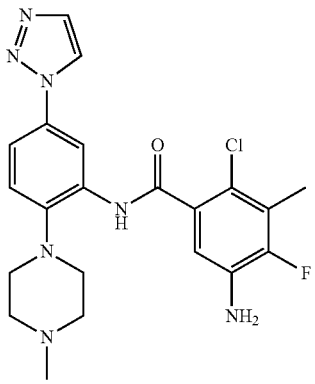 [SMILES: Cc1c(F)c(N)cc(C(=O)Nc2cc(-n3ccnn3)ccc2N2CCN(C)CC2)c1Cl]

Preparation of 5-amino-2-chloro-4-fluoro-3-methyl-N-(2-(4-methylpiperazin-1-group)-5-(1H-1,2,3-triazole-1-group) phenyl) benzamide (11)

Using the methods in application Example 1, replace ethyl propiolate with Trimethyl ethynyl silicon to obtain gray-white solid after three reaction steps. The yield of the three steps is 23.8%. $^1$H NMR (300 MHz, DMSO-d$_6$) δ8.76-8.68 (m, 2H), 8.49 (d, J=2.1 Hz, 1H), 8.18 (d, J=7.5 Hz, 1H), 7.27 (dd, J=7.5, 2.0 Hz, 1H), 6.82 (d, J=7.5 Hz, 1H), 6.75 (d, J=5.7 Hz, 1H), 4.15 (s, 2H), 3.20 (t, J=5.1 Hz, 4H), 2.98 (t, J=5.0 Hz, 4H), 2.60 (s, 3H), 2.39 (s, 3H). (EI-MS): 444.9 [M+Na]$^+$.

EXAMPLE 12

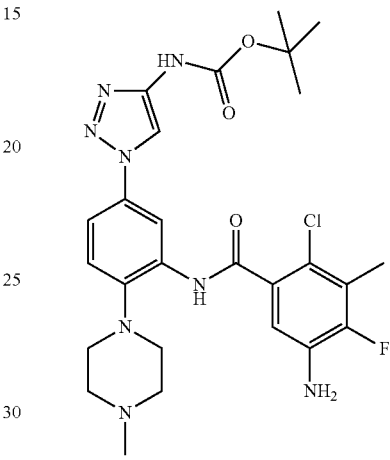

Tert-butyl(1-(3-(5-amino-2-chloro-4-fluoro-3-ethyl benzoylamino)-4-(4-methylpiperazin-1-group)phenyl)-1H-1,2,3-triazole-4-group) aminomethyl ester (12)

Using the methods in application Example 1, replace Methyl propiolate with tert-butyl ethynyl carbamate to obtain gray-white solid after three reaction steps. The yield of the three steps is 20.1%. $^1$H NMR (300 MHz, DMSO-d$_6$) δ8.70 (s, 1H), 8.59 (d, J=2.0 Hz, 1H), 8.08 (s, 1H), 7.25 (dd, J=7.5, 2.0 Hz, 1H), 7.18 (s, 1H), 6.80 (dd, J=19.7, 6.6 Hz, 2H), 4.17 (s, 2H), 3.20 (t, J=5.1 Hz, 4H), 2.98 (t, J=5.1 Hz, 4H), 2.60 (s, 3H), 2.39 (s, 3H), 1.50 (s, 9H). (EI-MS): 560.0 [M+Na]$^+$.

EXAMPLE 13

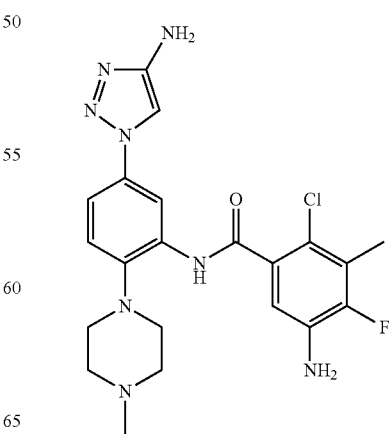

5-amino-N-(5-(4-amino-1H-1,2,3-triazole-1-group)-2-(4-methylpiperazin-1-group)phenyl)-2-chloro-4-fluoro-3-Methylbenzamide (13)

Dissolve Tert-butyl(1-(3-(5-amino-2-chloro-4-fluoro-3-ethyl benzoylamino)-4-(4-methylpiperazin-1-group)phenyl)-1H-1,2,3-triazole-4-group) aminomethyl ester (1.0 g, 2.2 mmol) in 20 mL dichloromethane, add 10 mL trifluoroacetate, stir for 1 h at room temperature, adjust pH=8-9 using saturated sodium bicarbonate, extract with dichloromethane, dry the organic phase with anhydrous sodium sulfate and dry with rotation to obtain grey solie. The yield is 87.3%. $^1$H NMR (300 MHz, DMSO-$d_6$) δ8.70 (s, 1H), 8.49 (d, J=2.0 Hz, 1H), 8.08 (s, 1H), 7.25 (dd, J=7.5, 2.0 Hz, 1H), 6.80 (d, J=7.5 Hz, 1H), 6.70 (d, J=5.7 Hz, 1H), 5.80 (s, 2H), 4.15 (s, 2H), 3.20 (t, J=5.3 Hz, 4H), 2.98 (t, J=5.2 Hz, 4H), 2.60 (s, 3H), 2.39 (s, 3H). (EI-MS): 459.9 [M+Na]$^+$.

EXAMPLE 14

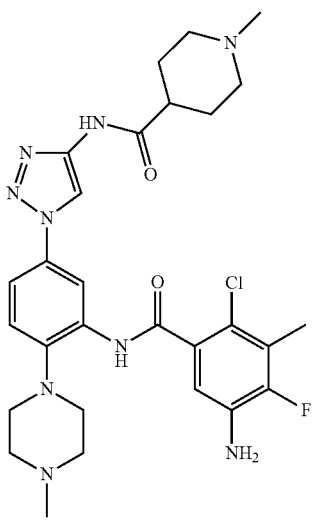 [SMILES: Cc1c(F)c(N)cc(C(=O)Nc2cc(-n3cc(NC(=O)C4CCN(C)CC4)nn3)ccc2N2CCN(C)CC2)c1Cl]

N-(1-(3-(5-amino-2-chloro-4-fluoro-3-ethyl benzoylamino)-4-(4-methylpiperazin-1-group)phenyl)-1H-1,2,3-triazole-4-group)-1-methylpiperidine-4-formamide (14)

Dissolve 5-amino-N-(5-(4-amino-1H-1,2,3-triazole-1-group)-2-(4-methylpiperazin-1-group)phenyl)-2-chloro-4-fluoro-3-Methylbenzamide (13) (0.2 g, 0.34 mmol) in 5 mL DMF, add BOP (0.30 g, 0.68 mmol), trimethylamine (0.09 mL, 0.68 mmol) and 1-Methylpiperidine-4-formic acid (97.3 mg, 0.68 mmol), stir for 4 h at room temperature. Dilute the reaction with 50 mL ethyl acetate, remove DMF by washing with saturated sodium chloride, dry the organic phase with anhydrous sodium sulfate, dry out the organic solvent with rotation to obtain raw product, isolate and purify with chromatography on silica gel column (dichloromethane:methanol=20:1) to obtain grey white solid. The yield is 73.9%. $^1$H NMR (300 MHz, DMSO-$d_6$) δ8.72-8.64 (m, 2H), 8.08 (s, 1H), 7.71 (s, 1H), 7.25 (dd, J=7.5.20 Hz, 1H), 6.87 (d, J=7.5 Hz, 1H), 6.69 (d, J=5.7 Hz, 1H), 4.16 (s, 2H), 3.20 (t, J=5.3 Hz, 4H), 3.05-2.95 (m, 6H), 2.60 (s, 3H), 2.50-2.45 (m, 1H), 2.39-2.37 (m, 6H), 2.14-2.09 (m, 2H), 2.05-1.98 (m, 2H), 1.81-1.70 (m, 2H). (EI-MS): 485.1 [M+Na]$^+$.

EXAMPLE 15

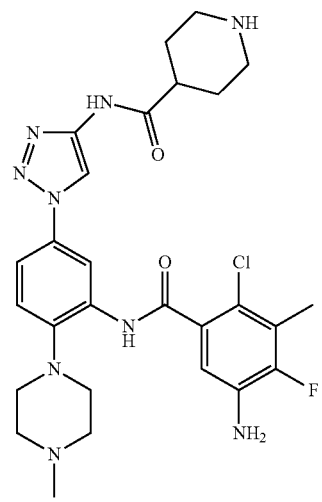 [SMILES: Cc1c(F)c(N)cc(C(=O)Nc2cc(-n3cc(NC(=O)C4CCNCC4)nn3)ccc2N2CCN(C)CC2)c1Cl]

N-(1-(3-(5-amino-2-chloro-4-fluoro-3-Methyl benzoylamino)-4-(4-methylpiperazin-1-group)phenyl)-1H-1,2,3-Triazopyridine-4-group) Piperidine-4-formamide (15)

Using the methods in application Example 14, replace 1-Methylpiperidine-4-formic acid with 4-piperidinic acid, grey while solid is obtained. The yield is 88.7%. $^1$H NMR (300 MHz, DMSO-$d_6$) δ8.70 (s, 1H), 8.55 (d, J=2.0 Hz, 1H), 8.08 (s, 1H), 7.71 (s, 1H), 7.26 (dd, J-7.5, 2.0 Hz, 1H), 6.80 (dd, J-23.8, 6.6 Hz, 2H), 4.15 (s, 2H), 3.27-3.17 (m, 6H), 2.98 (t, J=5.0 Hz, 4H), 2.82-2.65 (m, 3H), 2.60 (s, 3H), 2.39 (s, 3H), 2.03-1.96 (m, 2H), 1.74-1.69 (m, 2H), 1.22 (s, 1H). (EI-MS): 571.1 [M+Na]$^+$.

EXAMPLE 16

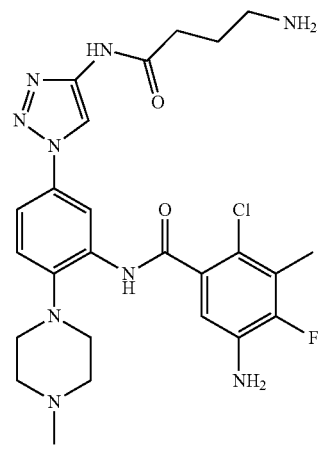 [SMILES: Cc1c(F)c(N)cc(C(=O)Nc2cc(-n3cc(NC(=O)CCCN)nn3)ccc2N2CCN(C)CC2)c1Cl]

5-amino-N-(5-(4-(4-Aminobutyrylamino)-1H-1,2,3-triazol-1-group)-2-(4-methylpiperazin-1-group)phenyl)-2-chloro-4-fluoro-3-methyl benzoylamino (16)

Using the methods in application Example 14, replace 1-Methylpiperidine-4-formic acid with γ-aminobutyric acid to obtain grey white solid. The yield is 88.7%. $^1$H NMR (300 MHz, DMSO-d$_6$) δ8.70 (s, 1H), 8.08 (s, 1H), 7.71 (s, 1H), 7.25 (dd, J=7.5, 2.0 Hz, 1H), 6.80 (dd, J=21.4, 6.6 Hz, 2H), 4.17 (s, 2H), 4.17 (s, 2H), 3.20 (t, J=5.1 Hz, 4H), 3.08-3.04 (m, 2H), 2.98 (t, J=5.1 Hz, 4H), 2.60 (s, 3H), 2.50 (t, J=8.2 Hz, 2H), 2.39 (s, 3H), 2.10-2.04 (m, 2H), 1.19 (s, 2H). (EI-MS): 571.1 [M+Na]$^+$.

EXAMPLE 17

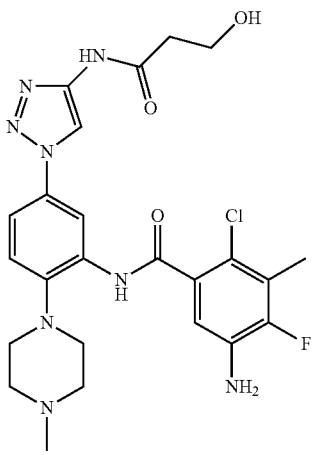 [SMILES: Cc1c(F)c(N)cc(C(=O)Nc2cc(-n3cc(NC(=O)CCO)nn3)ccc2N2CCN(C)CC2)c1Cl]

5-amino-2-chloro-4-fluoro-N-(5-(4-(3-Hydroxypropionylamino)-1H-1,2,3-triazol-1-group)-2-(4-methylpiperazin-1-group)phenyl)-3-methyl benzoylamino Using the methods in application Example 14, replace 1-Methylpiperidine-4-formic acid with 3-Hydroxypropionic acid to obtain grey white solid. The yield is 84.9%. $^1$H NMR (300 MHz, DMSO-d$_6$) δ8.70 (s, 1H), 8.57 (d, J=2.0 Hz, 1H), 8.08 (s, 1H), 7.71 (s, 1H), 7.25 (dd, J-7.5, 2.0 Hz, 1H), 6.80 (dd, J=21.8, 6.6 Hz, 2H), 4.36 (t, J=5.0 Hz, 1H), 4.17 (s, 2H), 3.83-3.79 (m, 2H), 3.20 (t, J=5.1 Hz, 4H), 2.98 (t, J=5.0 Hz, 4H), 2.60 (s, 3H), 2.39-2.35 (m, 5H). (EI-MS): 532.1 [M+Na]$^+$.

EXAMPLE 18

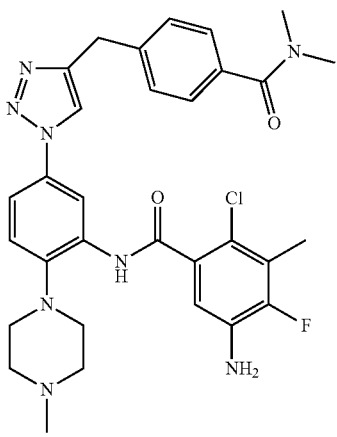 [SMILES: Cc1c(F)c(N)cc(C(=O)Nc2cc(-n3cc(Cc4ccc(C(=O)N(C)C)cc4)nn3)ccc2N2CCN(C)CC2)c1Cl]

5-amino-2-chloro-N-(5-(4-(4-(dimethylaminomethyl)benzyl)-1H-1,2,3-triazol-1-group)-2-(4-methylpiperazin-1-group group)phenyl)-4-fluoro-3-Methyl benzoyl (18)

Using the methods in application Example 1, replace methyl propiolate with N,N,-Dimethyl-4-(prop-2-yne-1-group) to obtain grey white solid in three steps. The yield of the three steps is 34.4%. $^1$H NMR (300 MHz, DMSO-d$_6$) δ8.70 (s, 1H), 8.49-8.44 (m, 2H), 7.74-7.68 (m, 2H), 7.56-7.50 (m, 2H), 7.26 (dd, J=7.4, 1.9 Hz, 1H), 6.75 (d, J=5.9 Hz, 1H), 4.16 (s, 2H), 3.88 (d, J=1.2 Hz, 2H), 3.20 (t, J=5.1 Hz, 4H), 3.0-2.95 (m, 10H), 2.60 (s, 3H), 2.38 (s, 3H). (EI-MS): 606.1 [M+Na]$^+$.

EXAMPLE 19

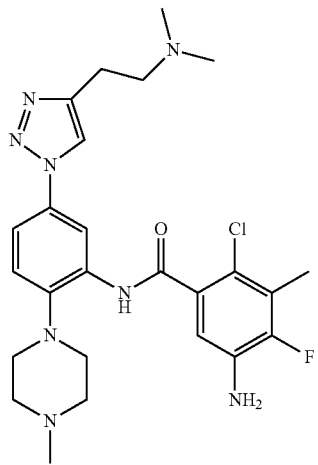 [SMILES: Cc1c(F)c(N)cc(C(=O)Nc2cc(-n3cc(CCN(C)C)nn3)ccc2N2CCN(C)CC2)c1Cl]

5-amino-2-chloro-N-(5-(4-(2-(Dimethylamino)ethyl)-1H-1,2,3-triazol-1-group)-2-(4-methylpiperazin-1-group group)phenyl)-4-fluoro-3-Methyl benzoyl (19)

Using the methods in application Example 1, replace methyl propiolate with N,N,-dimethyl-but-3-alkyne-1-amine to obtain grey white solid in three steps. The yield of the three steps is 31.6%. $^1$H NMR (300 MHz, DMSO-d$_6$) δ8.70 (s, 1H), 8.48 (d, J=2.0 Hz, 1H), 8.28 (s, 1H), 7.26 (dd, J=7.5, 2.0 Hz, 1H), 6.82 (d, J=7.5 Hz, 1H), 6.74 (d, J=5.7 Hz, 1H), 4.15 (s, 2H), 3.20 (t, J=5.1 Hz, 4H), 2.98 (t, J=5.0 Hz, 4H), 2.71-2.61 (m, 4H), 2.60 (s, 3H), 2.40-2.39 (m, 9H). (EI-MS): 606.1 [M+Na]$^+$.

EXAMPLE 20

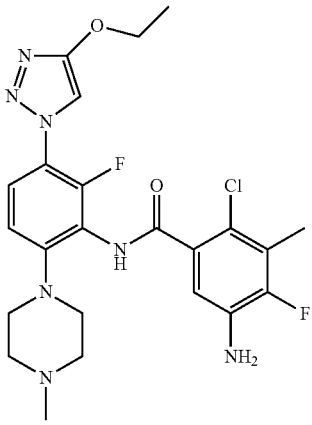 [SMILES: CCOc1cn(-c2ccc(N3CCN(C)CC3)c(NC(=O)c3cc(N)c(F)c(C)c3Cl)c2F)nn1]

5-amino-2-fluoro-N-(3-(4-Ethoxy-TH-1,2,3-triazol-1-group)-2-fluoro-6-(4-methylpiperazin-1-group)phenyl)-4-fluoro-3-Methyl benzoyl (20)

Using the methods in application Example 1, replace 4-fluoro-3-Nitroaniline with 2,4-difluoro-3-nitroaniline and methyl propiolate with ethyl ethynyl ether to obtain grey white solid in five steps. The yield of the five steps is 12.8%. $^1$H NMR (300 MHz, DMSO-$d_6$) δ8.70 (s, 1H), 7.98 (s, 1H), 7.30 (dd, J=7.5, 5.7 Hz, 1H), 6.74 (d, J=5.7 Hz, 1H), 6.59 (d, J=7.5 Hz, 1H), 4.76-4.72 (m, 2H), 4.15 (s, 2H), 3.20 (t, J=5.1 Hz, 4H), 2.98 (t, J=5.0 Hz, 4H), 2.60 (s, 3H), 2.39 (s, 3H), 1.56 (t, J=8.0 Hz, 3H). (EI-MS): 507.1 [M+Na]$^+$.

EXAMPLE 21

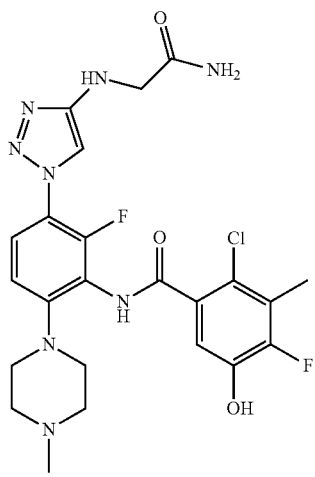 [SMILES: Cc1c(F)c(O)cc(C(=O)Nc2c(N3CCN(C)CC3)ccc(-n3cc(NCC(N)=O)nn3)c2F)c1Cl]

N-(3-(4-((2-amino-2-Oxoethyl)amino)-1H-1,2,3-triazol-1-group)-2-fluoro-6-(4-methylpiperazin-1-group)phenyl)-2-chloro-4-fluoro-5-hydroxl-3-Methyl benzoyl (21)

Using the method in application Example 1, replace 4-fluoro-3-Nitroaniline with 2,4-difluoro-3-nitroaniline, methyl propiolate with 2-(ethynylamino) Acetamide and 2-chloro-3-methyl-4-fluoro-5-Nitrobenzoyl chloride with 2-chloro-3-methyl-4-fluoro-5-hydroxybenzoyl chloride to obtain white solid in five reactions. The yield of the five reactions is 9.7%. $^1$H NMR (300 MHz, DMSO-$d_6$) δ8.70 (s, 1H), 8.07 (d, J=10.4 Hz, 2H), 7.34-7.24 (m, 2H), 6.59 (d, J=7.5 Hz, 1H), 5.98 (s, 2H), 5.93 (s, 1H), 4.03 (s, 2H), 3.20 (t, J=5.1 Hz, 4H), 2.98 (t, J=5.0 Hz, 4H), 2.60 (s, 3H), 2.38 (s, 3H). (EI-MS): 507.1 [M+Na]$^+$.

EXAMPLE 22

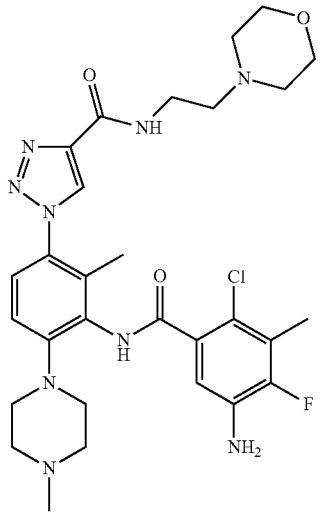 [SMILES: Cc1c(F)c(N)cc(C(=O)Nc2c(N3CCN(C)CC3)ccc(-n3cc(C(=O)NCCN4CCOCC4)nn3)c2C)c1Cl]

1-(3-(5-amino-2-chloro-4-fluoro-3-Methyl benzoylamino)-2-methyl-4-(4-methylpiperazin-1-group)phenyl)-N-(2-Morpholine ethyl)-1H-1,2,3-triazol-4-formamide (22)

Using the methods in application Example 3, replace 4-fluoro-3-Nitroaniline with 2-fluoro-4-methyl-3-Nitroaniline and Dimethylamino hydrochloride with N-(2-Aminoethyl) Morpholine to obtain grey white solid. The yield of the six steps is 8.8%. $^1$H NMR (300 MHz, DMSO-$d_6$) δ8.70 (s, 1H), 8.52 (s, 1H), 7.25 (s, 1H), 7.13 (d, J=7.5 Hz, 1H), 6.78 (d, J=5.7 Hz, 1H) 6.72 (d, J=7.5 Hz, 1H), 4.15 (s, 2H), 3.74 (t, J=4.7 Hz, 4H), 3.55-3.53 (m, 2H), 3.20 (t, J=5.1 Hz, 4H), 2.98 (t, J=5.1 Hz, 4H), 2.61-2.59 (m, 5H), 2.51 (t, J=4.7 Hz, 4H), 2.40-2.39 (m, 6H). (EI-MS): 615.1 [M+Na]$^+$.

EXAMPLE 23

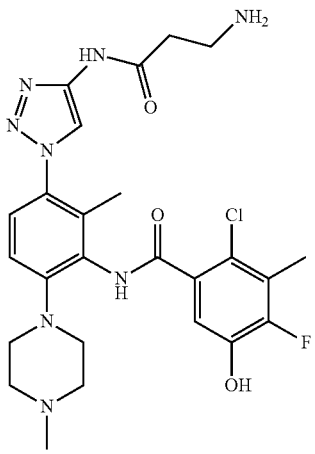

N-(3-(4-(3-Aminopropionylamino))-1H-1,2,3-triazol-1-group)-2-methyl-6-(4-methylpiperazin-1-group)phenyl)-2-chloro-4-fluoro-5-hydroxl-3-Methyl benzoyl (23)

Using the methods in application Example 14, replace 4-fluoro-3-Nitrobenzene with 2-fluoro-4-methyl-3-Nitrobenzene, 2-chloro-3-methyl-4-fluoro-5-Nitrobenzoyl chloride with 2-chloro-3-methyl-4-fluoro-5-Hydroxybenzoyl chloride, 1-methylpiperidine-4-carboxylic acid with β-Alanine to obtain white solid in six steps. The yield of the six steps is 7.2%. $^1$H NMR (300 MHz, DMSO-$d_6$) δ8.70 (s, 1H), 8.08 (s, 1H), 7.71 (s, 1H), 7.19 (d, J=7.5 Hz, 1H), 7.06 (d, J=5.7 Hz, 1H), 6.72 (d, J=7.5 Hz, 1H), 5.93 (s, 1H), 3.20 (t, J=5.1 Hz, 4H), 3.01-2.93 (m, 4H), 2.93-2.91 (m, 1H), 2.60 (s, 3H), 2.45 (s, 3H), 2.44-2.42 (m, 2H), 2.38 (s, 3H), 1.24 (s, 2H). (EI-MS): 615.1 [M+Na]$^+$.

EXAMPLE 24

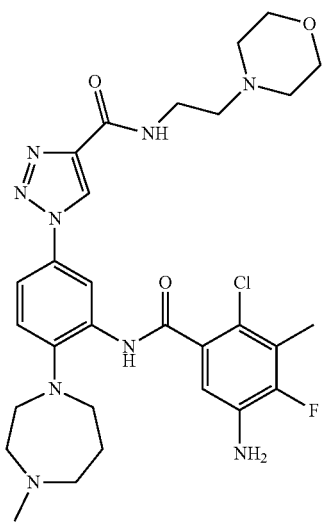 [SMILES: Cc1c(F)c(N)cc(C(=O)Nc2cc(-n3cc(C(=O)NCCN4CCOCC4)nn3)ccc2N2CCCN(C)CC2)c1Cl]

1-(3-(5-amino-2-chloro-4-fluoro-3-Methyl benzoylamino)-4-(4-methyl-1,4-Diazepane-1-group)phenyl)-N-(2-Morpholine ethyl)-1H-1,2,3-triazol-4-formamide (24)

Using the methods in application Examples 3, replace N-Methylpiperazine with N-Methyl homopiperazine and Dimethylamino hydrochloride with N-(2-aminoethyl)morpholine to obtain white solid. The yield of the six steps is 7.3%. $^1$H NMR (300 MHz, DMSO-$d_6$) δ8.79 (s, 1H), 8.70 (s, 1H), 7.31 (dd, J=7.5, 2.0 Hz, 1H), 7.25 (s, 1H), 6.83 (d, J=7.5 Hz, 1H), 6.70 (d, J=5.7 Hz, 1H), 4.16 (s, 2H), 3.74 (t, J=4.7 Hz, 4H), 3.60 (t, J=4.8 Hz, 2H), 3.55-3.53 (m, 2H), 3.46-3.44 (m, 2H), 2.91-2.89 (m, 2H), 2.61-2.58 (m, 4H), 2.52-2.50 (m, 4H), 2.39 (s, 3H), 2.31 (s, 3H), 1.64-1.60 (m, 2H). (EI-MS): 615.1 [M+Na]$^+$.

EXAMPLE 25

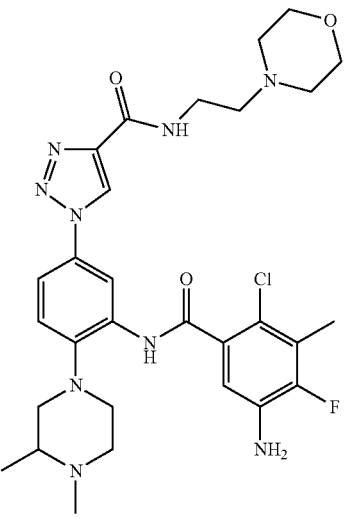 [SMILES: Cc1c(F)c(N)cc(C(=O)Nc2cc(-n3cc(C(=O)NCCN4CCOCC4)nn3)ccc2N2CCN(C)C(C)C2)c1Cl]

1-3-(5-amino-2-chloro-4-fluoro-3-Methyl benzoylamino)-4-(3,4-Dimethylpiperazine-1-group)phenyl)-N-(2-Morpholine ethyl)-1H-1,2,3-triazol-4-formamide (24)

Using the methods in application Example 3, replace N-Methylpiperazine with 1,2-Dimethylpiperazine and Dimethylamino hydrochloride with N-(2-aminoethyl)morpholine to obtain grey white solid. The yield of the six steps is 7.3%. $^1$H NMR (300 MHz, DMSO-$d_6$) δ8.80 (s, 1H), 8.70 (s, 1H), 8.54 (d, J=2.0 Hz, 1H), 7.31 (dd, J=7.5, 2.0 Hz, 1H), 7.25 (s, 1H), 6.81 (d, J=7.5 Hz, 1H), 6.70 (d, J=5.7 Hz, 1H), 4.18 4.04 (m, 7H), 3.66-3.53 (m, 2H), 3.35-3.31 (m, 1H), 3.20-3.07 (m, 4H), 2.93-2.87 (m, 1H), 2.73 2.58 (m, 2H), 2.51-2.37 (m, 7H), 2.34-2.20 (m, 3H), 1.16 (d, J=6.8 Hz, 3H). (EI MS): 615.1 [M+Na]$^+$.

What is claimed:

1. A compound of the formula (I) or a pharmaceutically acceptable salt thereof:

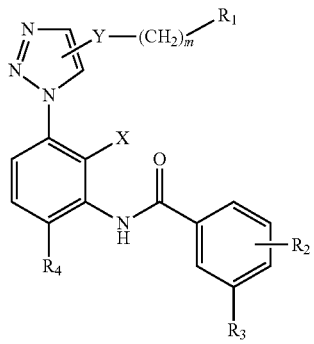

wherein X is hydrogen, methyl, methoxy or halogen;
Y is —CH$_2$—, —O—, —S—, —CO—, —CH$_2$O—, —NR$_5$—, —CONR$_6$— or —NR$_7$CO—, wherein R$_5$, R$_6$, or R$_7$ each independently is hydrogen, C$_1$-C$_4$ alkyl, C$_1$-C$_4$ haloalkyl, phenyl or substituted phenyl, the substituent is halogen, C$_1$-C$_4$ alkyl, C$_1$-C$_4$ alkoxy, amino, hydroxyl, thiol, carboxyl, cyano, trifluoromethyl or imidazolyl;
M is 0-6;
R$_1$ is hydrogen, amino, hydroxyl, thiol, carboxyl, cyano, —CONH$_2$, C$_1$-C$_4$ alkyl, C$_1$-C$_4$ alkoxy, phenyl, substituted phenyl, substituted or unsubstituted nitrogen- or oxygen-containing 3 to 7 membered heterocyclic ring, —NR$_8$COR$_9$, —CONR$_{10}$R$_{11}$ or —NR$_{10}$R$_{11}$, wherein R$_8$ is hydrogen, C$_1$-C$_4$ alkyl, C$_1$-C$_4$ haloalkyl, phenyl or substituted phenyl, R$_9$ is amino, hydroxyl, C$_1$-C$_4$ alkyl, C$_1$-C$_4$ alkoxy, phenyl or substituted phenyl, substituted or unsubstituted nitrogen- or oxygen-containing 3 to 7 membered heterocyclic ring, R$_{10}$, R$_{11}$ independently is hydrogen, C$_1$-C$_4$ alkyl, phenyl or substituted phenyl, substituted or unsubstituted nitrogen- or oxygen-containing 3 to 7 membered heterocyclic ring, or R$_{10}$ and R$_{11}$ are bonded to form nitrogen- or oxygen-containing 3 to 7 membered heterocyclic ring, wherein the substituent is halogen, C$_1$-C$_4$ alkyl, C$_1$-C$_4$ alkoxy, amino, hydroxyl, thiol, carboxyl, cyano, trifluoromethyl or imidazolyl;
R$_2$ is disubstituted or trisubstituted halogen, C$_1$-C$_4$ alkyl, C$_1$-C$_4$ alkoxy, trifluoromethyl, nitro or cyano;
R$_3$ is amino, methylamino, aminomethyl, hydroxyl, hydroxymethyl, thiol or —CONH$_2$;
R$_4$ is N-methylpiperazine, 1,2-dimethyl piperazine or N-methylhomopiperazine.

2. The compound according to claim 1, wherein X is hydrogen, fluorine, chlorine or methyl.

3. The compound of claim 1, wherein Y is —NR$_5$—, —CONR$_6$— or —NR$_7$CO—; R$_5$, R$_6$ or R$_7$ each independently is hydrogen, methyl, ethyl, propyl, cyclopropyl or isopropyl.

4. The compound of claim 1, wherein Y is —NR$_5$—, —CONR$_6$— or —NR$_7$CO—; R$_5$, R$_6$ or R$_7$ each independently is substituted phenyl, and the substituent is methyl, ethyl, isopropyl, t-butyl, cyclopropyl, methoxy, cyano, halogen, trifluoromethyl or imidazolyl.

5. The compound of claim 1, wherein said substituted or unsubstituted nitrogen- or oxygen-containing 3 to 7 membered heterocyclic ring is aziridine, azetidine, tetrahydrogen pyrrole, piperidine, cyclohexamide, lactam, tetrahydrofuran, tetrahydropyran, morpholine, 1,4-oxazaxane, hexahydropyridazine, imidazoline, pyrazolidine, piperazine, the substituent is methyl, ethyl, phenyl, hydroxyl, amino, hydroxymethyl, or aminomethyl, the substituent is halogen, C$_1$-C$_4$ alkyl, C$_1$-C$_4$ alkoxy, amino, hydroxyl, thiol, carboxyl, cyano, or trifluoromethyl.

6. The compound of claim 1, wherein R$_1$ is —NR$_8$COR$_9$, —CONR$_{10}$R$_{11}$ or —NR$_{10}$R$_{11}$, wherein R$_8$, R$_9$, R$_{10}$ or R$_{11}$ is C$_1$-C$_4$ alkyl.

7. The compound of claim 1, wherein R2 is trisubstitute, and the substituent is fluorine, chlorine, bromine, methyl, methoxy, nitro, trifluoromethyl or cyano.

8. A pharmaceutical composition comprising a compound of the formula (I) or a pharmaceutically acceptable salt thereof:

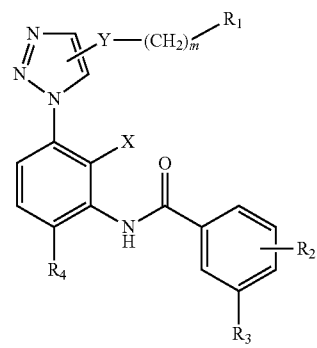

wherein X is hydrogen, methyl, methoxy or halogen;
Y is —CH$_2$—, —O—, —S—, —CO—, —CH$_2$O—, —NR$_5$—, —CONR$_6$— or —NR$_7$CO—, wherein R$_5$, R$_6$, or R$_7$ each independently is hydrogen, C$_1$-C$_4$ alkyl, C$_1$-C$_4$ haloalkyl, phenyl or substituted phenyl, the substituent is halogen, C$_1$-C$_4$ alkyl, C$_1$-C$_4$ alkoxy, amino, hydroxyl, thiol, carboxyl, cyano, trifluoromethyl or imidazolyl;
M is 0-6;
R$_1$ is hydrogen, amino, hydroxyl, thiol, carboxyl, cyano, —CONH$_2$, C$_1$-C$_4$ alkyl, C$_1$-C$_4$ alkoxy, phenyl, substituted phenyl, substituted or unsubstituted nitrogen- or oxygen-containing 3 to 7 membered heterocyclic ring, —NR$_8$COR$_9$, —CONR$_{10}$R$_{11}$ or —NR$_{10}$R$_{11}$, wherein R$_8$ is hydrogen, C$_1$-C$_4$ alkyl, C$_1$-C$_4$ haloalkyl, phenyl or substituted phenyl, R$_9$ is amino, hydroxyl, C$_1$-C$_4$ alkyl, C$_1$-C$_4$ alkoxy, phenyl or substituted phenyl, substituted or unsubstituted nitrogen- or oxygen-containing 3 to 7 membered heterocyclic ring, R$_{10}$, R$_{11}$ independently is hydrogen, C$_1$-C$_4$ alkyl, phenyl or substituted phenyl, substituted or unsubstituted nitrogen- or oxygen-containing 3 to 7 membered heterocyclic ring, or R$_{10}$ and R$_{11}$ are bonded to form nitrogen- or oxygen-containing 3 to 7 membered heterocyclic ring, wherein the substituent is halogen, C$_1$-C$_4$ alkyl, C$_1$-C$_4$ alkoxy, amino, hydroxyl, thiol, carboxyl, cyano, trifluoromethyl or imidazolyl;
R$_2$ is disubstituted or trisubstituted halogen, C$_1$-C$_4$ alkyl, C$_1$-C$_4$ alkoxy, trifluoromethyl, nitro or cyano;
R$_3$ is amino, methylamino, aminomethyl, hydroxyl, hydroxymethyl, thiol or —CONH$_2$;
R$_4$ is N-methylpiperazine, 1,2-dimethyl piperazine or N-methylhomopiperazine; and a pharmaceutically acceptable carrier.

9. A method of treating acute leukemia in a subject, the method comprising administering to said subject a compound of the formula (I) or a pharmaceutically acceptable salt thereof:

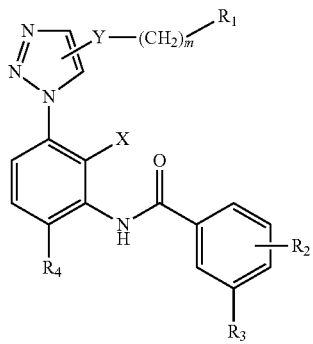

wherein X is hydrogen, methyl, methoxy or halogen;

Y is —$CH_2$—, —O—, —S—, —CO—, —$CH_2$O—, —$NR_5$—, —$CONR_6$— or —$NR_7CO$—, wherein $R_5$, $R_6$, or $R_7$ each independently is hydrogen, $C_1$-$C_4$ alkyl, $C_1$-$C_4$ haloalkyl, phenyl or substituted phenyl, the substituent is halogen, $C_1$-$C_4$ alkyl, $C_1$-$C_4$ alkoxy, amino, hydroxyl, thiol, carboxyl, cyano, trifluoromethyl or imidazolyl;

M is 0-6;

$R_1$ is hydrogen, amino, hydroxyl, thiol, carboxyl, cyano, —$CONH_2$, $C_1$-$C_4$ alkyl, $C_1$-$C_4$ alkoxy, phenyl, substituted phenyl, substituted or unsubstituted nitrogen- or oxygen-containing 3 to 7 membered heterocyclic ring, —$NR_8COR_9$, —$CONR_{10}R_{11}$ or —$NR_{10}R_{11}$, wherein $R_8$ is hydrogen, $C_1$-$C_4$ alkyl, $C_1$-$C_4$ haloalkyl, phenyl or substituted phenyl, $R_9$ is amino, hydroxyl, $C_1$-$C_4$ alkyl, $C_1$-$C_4$ alkoxy, phenyl or substituted phenyl, substituted or unsubstituted nitrogen- or oxygen-containing 3 to 7 membered heterocyclic ring, $R_{10}$, $R_{11}$ independently is hydrogen, $C_1$-$C_4$ alkyl, phenyl or substituted phenyl, substituted or unsubstituted nitrogen- or oxygen-containing 3 to 7 membered heterocyclic ring, or $R_{10}$ and $R_{11}$ are bonded to form nitrogen- or oxygen-containing 3 to 7 membered heterocyclic ring, wherein the substituent is halogen, $C_1$-$C_4$ alkyl, $C_1$-$C_4$ alkoxy, amino, hydroxyl, thiol, carboxyl, cyano, trifluoromethyl or imidazolyl;

$R_2$ is disubstituted or trisubstituted halogen, $C_1$-$C_4$ alkyl, $C_1$-$C_4$ alkoxy, trifluoromethyl, nitro or cyano;

$R_3$ is amino, methylamino, aminomethyl, hydroxyl, hydroxymethyl, thiol or —$CONH_2$;

$R_4$ is N-methylpiperazine, 1,2-dimethyl piperazine or N-methylhomopiperazine; and a pharmaceutically acceptable carrier.

10. The method of claim 9, wherein the acute leukemia is an acute leukemia having an MLL1 gene rearrangement type.

* * * * *